(12) United States Patent
Agarwal et al.

(10) Patent No.: US 12,409,247 B2
(45) Date of Patent: Sep. 9, 2025

(54) METHODS AND COMPOSITIONS FOR WOUND HEALING

(71) Applicant: Imbed Biosciences Inc., Middleton, WI (US)

(72) Inventors: Ankit Agarwal, Middleton, WI (US); Gaurav Pranami, Fitchburg, WI (US); Tyler B. Nelson, Madison, WI (US); Anna M. O'Keefe, Madison, WI (US); Nicholas L. Abbott, Middleton, WI (US); Eric Crawford, Madison, WI (US)

(73) Assignee: Imbed Biosciences Inc., Middleton, WI (US)

( * ) Notice: Subject to any disclaimer, the term of this patent is extended or adjusted under 35 U.S.C. 154(b) by 0 days.

(21) Appl. No.: 18/155,518

(22) Filed: Jan. 17, 2023

(65) Prior Publication Data

US 2024/0009342 A1    Jan. 11, 2024

Related U.S. Application Data

(63) Continuation of application No. 15/663,172, filed on Jul. 28, 2017, now Pat. No. 11,554,194.

(60) Provisional application No. 62/368,646, filed on Jul. 29, 2016.

(51) Int. Cl.
| | |
|---|---|
| A61L 15/44 | (2006.01) |
| A61F 13/02 | (2024.01) |
| A61K 9/70 | (2006.01) |
| A61K 31/155 | (2006.01) |
| A61K 31/167 | (2006.01) |
| A61K 31/19 | (2006.01) |
| A61K 31/381 | (2006.01) |
| A61K 31/445 | (2006.01) |
| A61K 31/4468 | (2006.01) |
| A61K 31/485 | (2006.01) |
| A61K 31/713 | (2006.01) |
| A61K 31/785 | (2006.01) |
| A61K 33/18 | (2006.01) |
| A61K 33/24 | (2019.01) |
| A61K 33/38 | (2006.01) |
| A61K 33/40 | (2006.01) |
| A61K 47/32 | (2006.01) |
| A61L 15/18 | (2006.01) |
| A61L 15/24 | (2006.01) |
| A61L 15/46 | (2006.01) |
| C12N 15/113 | (2010.01) |

(52) U.S. Cl.
CPC .......... *A61L 15/44* (2013.01); *A61F 13/0289* (2013.01); *A61K 9/7007* (2013.01); *A61K 9/7092* (2013.01); *A61K 31/155* (2013.01); *A61K 31/167* (2013.01); *A61K 31/19* (2013.01); *A61K 31/381* (2013.01); *A61K 31/445* (2013.01); *A61K 31/4468* (2013.01); *A61K 31/485* (2013.01); *A61K 31/713* (2013.01); *A61K 31/785* (2013.01); *A61K 33/18* (2013.01); *A61K 33/24* (2013.01); *A61K 33/38* (2013.01); *A61K 33/40* (2013.01); *A61K 47/32* (2013.01); *A61L 15/18* (2013.01); *A61L 15/46* (2013.01); *C12N 15/113* (2013.01); *A61F 2240/001* (2013.01); *A61L 2300/104* (2013.01); *A61L 2300/402* (2013.01); *A61L 2300/404* (2013.01); *A61L 2300/41* (2013.01); *A61L 2300/414* (2013.01); *A61L 2300/42* (2013.01); *A61L 2400/12* (2013.01); *A61L 2420/02* (2013.01); *A61L 2420/04* (2013.01); *A61L 2420/08* (2013.01); *C12N 2310/14* (2013.01)

(58) Field of Classification Search
CPC .............................. A61L 15/44; A61K 9/7092
See application file for complete search history.

(56) References Cited

U.S. PATENT DOCUMENTS

| | | | |
|---|---|---|---|
| 4,034,751 | A | 7/1977 | Hung |
| 5,660,692 | A | 8/1997 | Nesburn |
| 5,681,579 | A | 10/1997 | Freeman |
| 5,861,149 | A | 1/1999 | Ritter |
| 5,885,960 | A | 3/1999 | Nies |
| 6,095,148 | A | 8/2000 | Shastri |
| 6,165,514 | A * | 12/2000 | Bockman ............... A61K 33/06 424/650 |
| 6,559,119 | B1 | 5/2003 | Burgess |
| 6,696,077 | B2 | 2/2004 | Scherr |
| 6,716,452 | B1 | 4/2004 | Piccariello et al. |
| 6,852,353 | B2 | 2/2005 | Qiu |
| 6,855,860 | B2 | 2/2005 | Ruszczak et al. |
| 7,045,146 | B2 | 5/2006 | Caruso et al. |

(Continued)

FOREIGN PATENT DOCUMENTS

| | | |
|---|---|---|
| JP | 2012-515726 | 7/2012 |
| WO | WO 01/64258 | 9/2001 |

(Continued)

OTHER PUBLICATIONS

Extended EP Search Report, EP Patent Application No. 23195282.1, dated Feb. 9, 2024, 8 pages.
Agarwal et al., "Transferrable Antibacterial Nanofilms of Silver-Nanoparticles for Artificial Skin" Abstract Only; 22nd Annual Meeting of Wound Healing Society, Georgia World Congress Center, Apr. 2012, 1 page.
Agarwal, A., et al., "Surfaces modified with nanometer-thick silver-impregnate d polymeric films that kill bacteria but support growth of mammalian cells," Biomaterials, Feb. 2010 (online published on Oct. 28, 2009), vol. 31, No. 4, pp. 680-690.

(Continued)

*Primary Examiner* — Cachet I Proctor
(74) *Attorney, Agent, or Firm* — Casimir Jones, S.C.; J. Mitchell Jones

(57) ABSTRACT

The present invention relates to large scale manufacture of nanoscale microsheets for use in applications such as wound healing or modification of a biological or medical surface.

6 Claims, No Drawings

Specification includes a Sequence Listing.

(56) References Cited

U.S. PATENT DOCUMENTS

| | | |
|---|---|---|
| 7,118,761 B2 | 10/2006 | Canada et al. |
| 7,223,327 B2 | 5/2007 | Schlenoff |
| 7,595,355 B2 | 9/2009 | Trogolo |
| 7,758,892 B1 | 7/2010 | Chen |
| 7,884,090 B2 | 2/2011 | Bonner et al. |
| 2003/0078532 A1 | 4/2003 | Ruszczak et al. |
| 2003/0087111 A1 | 5/2003 | Hubbell et al. |
| 2003/0157260 A1 | 8/2003 | Rubner |
| 2004/0149572 A1 | 8/2004 | Schlenoff et al. |
| 2004/0214326 A1 | 10/2004 | Cousins et al. |
| 2005/0249791 A1 | 11/2005 | Hobbs et al. |
| 2005/0249818 A1 | 11/2005 | Sawan |
| 2007/0129792 A1 | 6/2007 | Picart |
| 2007/0154448 A1 | 7/2007 | Reid et al. |
| 2008/0131493 A1 | 6/2008 | Matloub |
| 2008/0206293 A1* | 8/2008 | Toreki ............... A61P 31/04 514/642 |
| 2008/0234618 A1* | 9/2008 | Baldock ............. A61L 15/44 602/44 |
| 2008/0286346 A1 | 11/2008 | Goerl et al. |
| 2009/0263468 A1 | 10/2009 | McAnulty |
| 2010/0069850 A1* | 3/2010 | Fabo ................. A61M 1/87 604/180 |
| 2011/0189287 A1* | 8/2011 | Abbott ............... B82Y 5/00 435/325 |
| 2011/0189493 A1 | 8/2011 | Ott et al. |
| 2012/0027837 A1 | 2/2012 | Demuth et al. |
| 2014/0377331 A1 | 12/2014 | Ryu et al. |
| 2015/0140055 A1* | 5/2015 | Schlenoff ........... A61L 15/425 424/411 |
| 2015/0283287 A1 | 10/2015 | Agarwal et al. |
| 2016/0030624 A1 | 2/2016 | Abbott et al. |
| 2016/0101207 A1 | 4/2016 | Parsons et al. |

FOREIGN PATENT DOCUMENTS

| | | | |
|---|---|---|---|
| WO | 2004/056404 | 7/2004 | |
| WO | WO 2005/018543 | 3/2005 | |
| WO | WO 2005/025548 | 3/2005 | |
| WO | WO 2007/035296 | 3/2005 | |
| WO | WO 2005/058199 | 6/2005 | |
| WO | WO 2007/108775 | 9/2007 | |
| WO | WO 2009/097508 | 8/2009 | |
| WO | WO 2010/083589 | 7/2010 | |
| WO | WO-2014074503 A1 * | 5/2014 | ............. A61F 13/02 |
| WO | WO 2016/019279 | 2/2016 | |

OTHER PUBLICATIONS

Atiyeh, et al., "Effect of silver on burn wound infection control and healing: Review of the Literature," Burns, Butterworth Heinemann, GB, vol. 33, No. 2, Feb. 3, 2007, pp. 139-148.

Elbert, Donald L., et al., "Thin Polymer Layers Formed by Polyelectrolyte Multilayer Techniques on Biological Surfaces," Langmuir (1999) 15, pp. 5355-5362.

EP Office Action, EP Patent Application No. 09748927.2, mailed Sep. 16, 2015.

EP Supplemental Search mailed Feb. 26, 2013, EP Patent Application No. 09 748 927.2.

Grunlan et al., "Antimicrobial Behavior of Polyelectrolyte Multilayer Flims Containing Cetrimide and Silver." Biomacromolecules, vol. 6, No. 2, 2005, pp. 1149-1153.

Huang, et al., "Chitosan mediated assembly of gold nanoparticles multilayer," Colloids and Surfaces A: Physicochem. Eng. Aspects 226 (2003) pp. 77-86.

International Search Report and Written Opinion, International Patent Application No. PCT/US2009/032607, mailed Aug. 12, 2009.

International Search Report and Written Opinion, International Patent Application No. PCT/US2011/024344, mailed Oct. 18, 2011.

International Search Report and Written Opinion, International Patent Application No. PCT/US2013/068463, mailed Feb. 5, 2014, 24 pages.

International Search Report and Written Opinion, International Patent Application No. PCT/US2017/044418, mailed Oct. 5, 2017.

Lee, Daeyeon, et al., "Antibacterial properties of Ag nanoparticle loaded multilayers and formation of magnetically directed antibacterial microparticles," Langmuir, American Chemical Society, New York, NY US, vol. 21, No. 21, Oct. 11, 2005, pp. 9651-9659.

Supplemental EP Search Report, EP Patent Application No. 11742789.8, mailed Feb. 16, 2016.

Supplemental EP Search Report, EP Patent Application No. 11742789.8, mailed Nov. 2, 2015.

Supplemental EP Search Report, EP Patent Application No. 17835355.3, mailed Apr. 1, 2020.

Thompson, Michael T., et al., "Tuning compliance of nanoscale polyelectrolyte multilayers to modulate cell adhesion," Biomaterials 26 (2005), pp. 6836-6845.

Wang, Tom C., et al., "Polyelectrolyte Multilayer Nanoreactors for Preparing Silver Nanoparticle Composites: Controlling Metal Concentration and Nanoparticle Size," Langmuir, vol. 18, No. 8, Apr. 1, 2002, pp. 3370-3375.

* cited by examiner

SEQUENCE LISTING

```
Sequence total quantity: 95
SEQ ID NO: 1              moltype = AA  length = 64
FEATURE                   Location/Qualifiers
source                    1..64
                          mol_type = protein
                          organism = Bos taurus
SEQUENCE: 1
MRLHHLLLAL LFLVLSAGSG FTQGVRNSQS CRRNKGICVP IRCPGSMRQI GTCLGAQVKC  60
CRRK                                                              64

SEQ ID NO: 2              moltype = AA  length = 24
FEATURE                   Location/Qualifiers
source                    1..24
                          mol_type = protein
                          organism = Xenopus laevis
SEQUENCE: 2
GVLSNVIGYL KKLGTGALNA VLKQ                                        24

SEQ ID NO: 3              moltype = AA  length = 81
FEATURE                   Location/Qualifiers
source                    1..81
                          mol_type = protein
                          organism = Xenopus laevis
SEQUENCE: 3
MYKGIFLCVL LAVICANSLA TPSSDADEDN DEVERYVRGW ASKIGQTLGK IAKVGLKELI  60
QPKREAMLRS AEAQGKRPWI L                                           81

SEQ ID NO: 4              moltype = AA  length = 303
FEATURE                   Location/Qualifiers
source                    1..303
                          mol_type = protein
                          organism = Xenopus laevis
SEQUENCE: 4
MFKGLFICSL IAVICANALP QPEASADEDM DEREVRGIGK FLHSAGKFGK AFVGEIMKSK  60
RDAEAVGPEA FADEDLDERE VRGIGKFLHS AKKFGKAFVG EIMNSKRDAE AVGPEAFADE 120
DLDEREVRGI GKFLHSAKKF GKAFVGEIMN SKRDAEAVGP EAFADEDLDE REVRGIGKFL 180
HSAKKFGKAF VGEIMNSKRD AEAVGPEAFA DEDFDEREVR GIGKFLHSAK KFGKAFVGEI 240
MNSKRDAEAV GPEAFADEDL DEREVRGIGK FLHSAKKFGK AFVGEIMNSK RDAEAVDDRR 300
WVE                                                              303

SEQ ID NO: 5              moltype = AA  length = 17
FEATURE                   Location/Qualifiers
source                    1..17
                          mol_type = protein
                          organism = Tachypleus gigas
SEQUENCE: 5
KWCFRVCYRG ICYRRCR                                                17
```

```
SEQ ID NO: 6              moltype = AA   length = 17
FEATURE                   Location/Qualifiers
source                    1..17
                          mol_type = protein
                          organism = Tachypleus gigas
SEQUENCE: 6
RWCFRVCYRG ICYRKCR                                                    17

SEQ ID NO: 7              moltype = AA   length = 129
FEATURE                   Location/Qualifiers
source                    1..129
                          mol_type = protein
                          organism = Bufo gargarizans
SEQUENCE: 7
MSGRGKQGGK VRAKAKTRSS RAGLQFPVGR VHRLLRKGNY AQRVGAGAPV YLAAVLEYLT     60
AEILELAGNA ARDNKKTRII PRHLQLAVRN DEELNKLLGG VTIAQGGVLP NIQAVLLPKT    120
ESSKPAKSK                                                            129

SEQ ID NO: 8              moltype = AA   length = 21
FEATURE                   Location/Qualifiers
source                    1..21
                          mol_type = protein
                          organism = Bufo gargarizans
SEQUENCE: 8
TRSSRAGLQF PVGRVHRLLR K                                               21

SEQ ID NO: 9              moltype = AA   length = 63
FEATURE                   Location/Qualifiers
source                    1..63
                          mol_type = protein
                          organism = Bombyx mori
SEQUENCE: 9
MNFVRILSFV FALVLALGAV SAAPEPRWKL FKKIEKVGRN VRDGLIKAGP AIAVIGQAKS     60
LGK                                                                   63

SEQ ID NO: 10             moltype = AA   length = 63
FEATURE                   Location/Qualifiers
source                    1..63
                          mol_type = protein
                          organism = Bombyx mori
SEQUENCE: 10
MNFAKILSFV FALVLALSMT SAAPEPRWKI FKKIEKMGRN IRDGIVKAGP AIEVLGSAKA     60
IGK                                                                   63

SEQ ID NO: 11             moltype = AA   length = 63
FEATURE                   Location/Qualifiers
source                    1..63
                          mol_type = protein
                          organism = Drosophila melanogaster
SEQUENCE: 11
MNFYKIFVFV ALILAISIGQ SEAGWLKKLG KRIERIGQHT RDATIQGLGI AQQAANVAAT     60
ARG                                                                   63

SEQ ID NO: 12             moltype = AA   length = 31
FEATURE                   Location/Qualifiers
source                    1..31
                          mol_type = protein
                          organism = Sus scrofa
SEQUENCE: 12
SWLSKTAKKL ENSAKKRISE GIAIAIQGGP R                                    31

SEQ ID NO: 13             moltype = AA   length = 13
FEATURE                   Location/Qualifiers
source                    1..13
                          mol_type = protein
                          organism = Bos taurus
SEQUENCE: 13
ILPWKWPWWP WRR                                                        13

SEQ ID NO: 14             moltype = AA   length = 34
FEATURE                   Location/Qualifiers
source                    1..34
                          mol_type = protein
                          organism = Lactococcus lactis
SEQUENCE: 14
ITSISLCTPG CKTGALMGCN MKTATCHCSI HVSK                                 34

SEQ ID NO: 15             moltype = AA   length = 20
```

```
FEATURE                 Location/Qualifiers
source                  1..20
                        mol_type = protein
                        organism = Lithobates catesbeianus
SEQUENCE: 15
FLGGLIKIVP AMICAVTKKC                                                      20

SEQ ID NO: 16           moltype = AA  length = 25
FEATURE                 Location/Qualifiers
source                  1..25
                        mol_type = protein
                        organism = Bos taurus
SEQUENCE: 16
FKCRRWQWRM KKLGAPSITC VRRAF                                                25

SEQ ID NO: 17           moltype = AA  length = 19
FEATURE                 Location/Qualifiers
source                  1..19
                        mol_type = protein
                        organism = Sus scrofa
SEQUENCE: 17
RGGRLCYCRR RFCVCVGRX                                                       19

SEQ ID NO: 18           moltype = AA  length = 16
FEATURE                 Location/Qualifiers
source                  1..16
                        mol_type = protein
                        organism = Sus scrofa
SEQUENCE: 18
GGRLCYCRRR FCICVG                                                          16

SEQ ID NO: 19           moltype = AA  length = 51
FEATURE                 Location/Qualifiers
source                  1..51
                        mol_type = protein
                        organism = Homo sapiens
SEQUENCE: 19
MKFFVFALIL ALMLSMTGAD SHAKRHHGYK RKFHEKHHSH RGYRSNYLYD N                    51

SEQ ID NO: 20           moltype = AA  length = 38
FEATURE                 Location/Qualifiers
source                  1..38
                        mol_type = protein
                        organism = Macaca fascicularis
SEQUENCE: 20
DSHEERHHGR HGHHKYGRKF HEKHHSHRGY RSNYLYDN                                   38

SEQ ID NO: 21           moltype = AA  length = 33
FEATURE                 Location/Qualifiers
source                  1..33
                        mol_type = protein
                        organism = Phyllomedusa sauvagii
SEQUENCE: 21
ALWKTMLKKL GTMALHAGKA ALGAAADTIS QTQ                                        33

SEQ ID NO: 22           moltype = AA  length = 34
FEATURE                 Location/Qualifiers
source                  1..34
                        mol_type = protein
                        organism = Phyllomedusa sauvagii
SEQUENCE: 22
ALWFTMLKKL GTMALHAGKA ALGAAANTIS QGTQ                                       34

SEQ ID NO: 23           moltype = AA  length = 30
FEATURE                 Location/Qualifiers
source                  1..30
                        mol_type = protein
                        organism = Phyllomedusa sauvagii
SEQUENCE: 23
ALWKNMLKGI GKLAGKAALG AVKKLVGAES                                            30

SEQ ID NO: 24           moltype = AA  length = 21
FEATURE                 Location/Qualifiers
source                  1..21
                        mol_type = protein
                        organism = Misgurnus anguillicaudatus
SEQUENCE: 24
RQRVEELSKF SKKGAAARRR K                                                     21
```

```
SEQ ID NO: 25           moltype = AA  length = 27
FEATURE                 Location/Qualifiers
source                  1..27
                        mol_type = protein
                        organism = Apis mellifera
SEQUENCE: 25
GIGAVLKVLT TGLPALISWI SRKKRQQ                                         27

SEQ ID NO: 26           moltype = AA  length = 33
FEATURE                 Location/Qualifiers
source                  1..33
                        mol_type = protein
                        organism = Pardachirus pavoninus
SEQUENCE: 26
GFFALIPKII SSPLFKTLLS AVGSALSSSG EQE                                  33

SEQ ID NO: 27           moltype = AA  length = 33
FEATURE                 Location/Qualifiers
source                  1..33
                        mol_type = protein
                        organism = Pardachirus pavoninus
SEQUENCE: 27
GFFALIPKII SSPIFKTLLS AVGSALSSSG GQE                                  33

SEQ ID NO: 28           moltype = AA  length = 176
FEATURE                 Location/Qualifiers
source                  1..176
                        mol_type = protein
                        organism = Bos taurus
SEQUENCE: 28
METQRASLSL GRCSLWLLLL GLVLPSASAQ ALSYREAVLR AVDQFNERSS EANLYRLLEL     60
DPTPNDDLDP GTRKPVSFRV KETDCPRTSQ QPLEQCDFKE NGLVKQCVGT VTLDPSNDQF    120
DINCNELQSV RFRPPIRRPP IRPPFYPPFR PPIRPPIFPP IRPPFRPPLG PFPGRR        176

SEQ ID NO: 29           moltype = AA  length = 155
FEATURE                 Location/Qualifiers
source                  1..155
                        mol_type = protein
                        organism = Bos taurus
SEQUENCE: 29
METPRASLSL GRWSLWLLLL GLALPSASAQ ALSYREAVLR AVDQLNEQSS EPNIYRLLEL     60
DQPPQDDEDP DSPKRVSFRV KETVCSRTTQ QPPEQCDFKE NGLLKRCEGT VTLDQVRGNF    120
DITCNNHQSI RITKQPWAPP QAARLCRIVV IRVCR                               155

SEQ ID NO: 30           moltype = AA  length = 29
FEATURE                 Location/Qualifiers
source                  1..29
                        mol_type = protein
                        organism = Ceratitis capitata
SEQUENCE: 30
SIGSALKKAL PVAKKIGKIA LPIAKAALP                                       29

SEQ ID NO: 31           moltype = AA  length = 29
FEATURE                 Location/Qualifiers
source                  1..29
                        mol_type = protein
                        organism = Ceratitis capitata
SEQUENCE: 31
SIGSAFKKAL PVAKKIGKAA LPIAKAALP                                       29

SEQ ID NO: 32           moltype = AA  length = 170
FEATURE                 Location/Qualifiers
source                  1..170
                        mol_type = protein
                        organism = Homo sapiens
SEQUENCE: 32
MKTQRNGHSL GRWSLVLLLL GLVMPLAIIA QVLSYKEAVL RAIDGINQRS SDANLYRLLD     60
LDPRPTMDGD PDTPKPVSFT VKETVCPRTT QQSPEDCDFK KDGLVKRCMG TVTLNQARGS    120
FDISCDKDNK RFALLGDFFR KSKEKIGKEF KRIVQRIKDF LRNLVPRTES               170

SEQ ID NO: 33           moltype = AA  length = 170
FEATURE                 Location/Qualifiers
source                  1..170
                        mol_type = protein
                        organism = Equus caballus
SEQUENCE: 33
METQRNTRCL GRWSPLLLLL GLVIPPATTQ ALSYKEAVLR AVDGLNQRSS DENLYRLLEL     60
DPLPKGDKDS DTPKPVSFMV KETVCPRIMK QTPEQCDFKE NGLVKQCVGT VILDPVKDYF    120
DASCDEPQRV KRFHSVGSLI QRHQQMIRDK SEATRHGIRI ITRPKLLLAS                170
```

-continued

```
SEQ ID NO: 34           moltype = AA   length = 159
FEATURE                 Location/Qualifiers
source                  1..159
                        mol_type = protein
                        organism = Bos taurus
SEQUENCE: 34
METQRASLSL GRWSLWLLLL GLALPSASAQ ALSYREAVLR AVDQLNEKSS EANLYRLLEL    60
DPPPKEDDEN PNIPKPVSFR VKETVCPRTS QQSPEQCDFK ENGLLKECVG TVTLDQVGSN   120
FDITCAVPQS VGGLRSLGRK ILRAWKKYGP IIVPIIRIG                          159

SEQ ID NO: 35           moltype = AA   length = 156
FEATURE                 Location/Qualifiers
source                  1..156
                        mol_type = protein
                        organism = Equus caballus
SEQUENCE: 35
METQRNTRCL GRWSPLLLLL GLVIPPATTQ ALSYKEAVLR AVDGLNQRSS DENLYRLLEL    60
DPLPKGDKDS DTPKPVSFMV KETVCPRIMK QTPEQCDFKE NGLVKQCVGT VILGPVKDHF   120
DVSCGEPQRV KRFGRLAKSF LRMRILLPRR KILLAS                             156

SEQ ID NO: 36           moltype = AA   length = 160
FEATURE                 Location/Qualifiers
source                  1..160
                        mol_type = protein
                        organism = Ovis aries
SEQUENCE: 36
METQRASLSL GRCSLWLLLL GLALPSASAQ VLSYREAVLR AADQLNEKSS EANLYRLLEL    60
DPPPKQDDEN SNIPKPVSFR VKETVCPRTS QQPAEQCDFK ENGLLKECVG TVTLDQVRNN   120
FDITCAEPQS VRGLRRLGRK IAHGVKKYGP TVLRIIRIAG                         160

SEQ ID NO: 37           moltype = AA   length = 12
FEATURE                 Location/Qualifiers
source                  1..12
                        mol_type = protein
                        organism = Bos taurus
SEQUENCE: 37
RLCRIVVIRV CR                                                        12

SEQ ID NO: 38           moltype = AA   length = 30
FEATURE                 Location/Qualifiers
source                  1..30
                        mol_type = protein
                        organism = Homo sapiens
SEQUENCE: 38
ACYCRIPACI AGERRYGTCI YQGRLWAFCC                                     30

SEQ ID NO: 39           moltype = AA   length = 29
FEATURE                 Location/Qualifiers
source                  1..29
                        mol_type = protein
                        organism = Homo sapiens
SEQUENCE: 39
CYCRIPACIA GERRYGTCIY QGRLWAFCC                                      29

SEQ ID NO: 40           moltype = AA   length = 30
FEATURE                 Location/Qualifiers
source                  1..30
                        mol_type = protein
                        organism = Homo sapiens
SEQUENCE: 40
DCYCRIPACI AGERRYGTCI YQGRLWAFCC                                     30

SEQ ID NO: 41           moltype = AA   length = 33
FEATURE                 Location/Qualifiers
source                  1..33
                        mol_type = protein
                        organism = Homo sapiens
SEQUENCE: 41
VCSCRLVFCR RTELRVGNCL IGGVSFTYCC TRV                                 33

SEQ ID NO: 42           moltype = AA   length = 33
FEATURE                 Location/Qualifiers
source                  1..33
                        mol_type = protein
                        organism = Oryctolagus cuniculus
SEQUENCE: 42
VVCACRRALC LPRERRAGFC RIRGRIHPLC CRR                                 33
```

| | | |
|---|---|---|
| SEQ ID NO: 43 | moltype = AA length = 33 | |
| FEATURE | Location/Qualifiers | |
| source | 1..33 | |
| | mol_type = protein | |
| | organism = Oryctolagus cuniculus | |
| SEQUENCE: 43 | | |
| VVCACRRALC LPLERRAGFC RIRGRIHPLC CRR | | 33 |
| | | |
| SEQ ID NO: 44 | moltype = AA length = 34 | |
| FEATURE | Location/Qualifiers | |
| source | 1..34 | |
| | mol_type = protein | |
| | organism = Oryctolagus cuniculus | |
| SEQUENCE: 44 | | |
| GICACRRRFC PNSERFSGYC RVNGARYVRC CSRR | | 34 |
| | | |
| SEQ ID NO: 45 | moltype = AA length = 34 | |
| FEATURE | Location/Qualifiers | |
| source | 1..34 | |
| | mol_type = protein | |
| | organism = Oryctolagus cuniculus | |
| SEQUENCE: 45 | | |
| GRCVCRKQLL CSYRERRIGD CKIRGVRFPF CCPR | | 34 |
| | | |
| SEQ ID NO: 46 | moltype = AA length = 34 | |
| FEATURE | Location/Qualifiers | |
| source | 1..34 | |
| | mol_type = protein | |
| | organism = Oryctolagus cuniculus | |
| SEQUENCE: 46 | | |
| VSCTCRRFSC GFGERASGSC TVNGGVRHTL CCRR | | 34 |
| | | |
| SEQ ID NO: 47 | moltype = AA length = 33 | |
| FEATURE | Location/Qualifiers | |
| source | 1..33 | |
| | mol_type = protein | |
| | organism = Oryctolagus cuniculus | |
| SEQUENCE: 47 | | |
| VFCTCRGFLC GSGERASGSC TINGVRHTLC CRR | | 33 |
| | | |
| SEQ ID NO: 48 | moltype = AA length = 32 | |
| FEATURE | Location/Qualifiers | |
| source | 1..32 | |
| | mol_type = protein | |
| | organism = Rattus norvegicus | |
| SEQUENCE: 48 | | |
| VTCYCRRTRC GFRERLSGAC GYRGRIYRLC CR | | 32 |
| | | |
| SEQ ID NO: 49 | moltype = AA length = 30 | |
| FEATURE | Location/Qualifiers | |
| source | 1..30 | |
| | mol_type = protein | |
| | organism = Rattus norvegicus | |
| SEQUENCE: 49 | | |
| CSCRYSSCRF GERLLSGACR LNGRIYRLCC | | 30 |
| | | |
| SEQ ID NO: 50 | moltype = AA length = 31 | |
| FEATURE | Location/Qualifiers | |
| source | 1..31 | |
| | mol_type = protein | |
| | organism = Rattus norvegicus | |
| SEQUENCE: 50 | | |
| ACTCRIGACV SGERLTGACG LNGRIYRLCC R | | 31 |
| | | |
| SEQ ID NO: 51 | moltype = AA length = 31 | |
| FEATURE | Location/Qualifiers | |
| source | 1..31 | |
| | mol_type = protein | |
| | organism = Cavia porcellus | |
| SEQUENCE: 51 | | |
| RRCICTTRTC RFPYRRLGTC IFQNRVYTFC C | | 31 |
| | | |
| SEQ ID NO: 52 | moltype = AA length = 67 | |
| FEATURE | Location/Qualifiers | |
| source | 1..67 | |
| | mol_type = protein | |
| | organism = Homo sapiens | |
| SEQUENCE: 52 | | |
| MRIHYLLFAL LFLFLVPVPG HGGIINTLQK YYCRVRGGRC AVLSCLPKEE QIGKCSTRGR | | 60 |

```
                                              -continued
KCCRRKK                                                                      67

SEQ ID NO: 53            moltype = AA   length = 18
FEATURE                  Location/Qualifiers
source                   1..18
                         mol_type = protein
                         organism = Macaca mulatta
SEQUENCE: 53
RCICTRGFCR CLCRRGVC                                                          18

SEQ ID NO: 54            moltype = AA   length = 78
FEATURE                  Location/Qualifiers
source                   1..78
                         mol_type = protein
                         organism = Helianthus annuus
SEQUENCE: 54
MKSSMKMFAA LLLVVMCLLA NEMGGPLVVE ARTCESQSHK FKGTCLSDTN CANVCHSERF             60
SGGKCRGFRR RCFCTTHC                                                          78

SEQ ID NO: 55            moltype = AA   length = 78
FEATURE                  Location/Qualifiers
source                   1..78
                         mol_type = protein
                         organism = Helianthus annuus
SEQUENCE: 55
MKSSMKMFAA LLLVVMCLLA NEMGGPLVVE ARTCESQSHK FKGTCLSDTN CANVCHSERF             60
SGGKCRGFRR RCFCTTHC                                                          78

SEQ ID NO: 56            moltype = AA   length = 30
FEATURE                  Location/Qualifiers
source                   1..30
                         mol_type = protein
                         organism = Macaca mulatta
SEQUENCE: 56
ACYCRIPACL AGERRYGTCF YMGRVWAFCC                                              30

SEQ ID NO: 57            moltype = AA   length = 37
FEATURE                  Location/Qualifiers
source                   1..37
                         mol_type = protein
                         organism = Androctonus australis
SEQUENCE: 57
GFGCPFNQGA CHRHCRSIRR RGGYCAGLFK QTCTCYR                                      37

SEQ ID NO: 58            moltype = AA   length = 38
FEATURE                  Location/Qualifiers
source                   1..38
                         mol_type = protein
                         organism = Mytilus galloprovincialis
SEQUENCE: 58
GFGCPNNYQC HRHCKSIPGR CGGYCGGXHR LRCTCYRC                                     38

SEQ ID NO: 59            moltype = AA   length = 54
FEATURE                  Location/Qualifiers
source                   1..54
                         mol_type = protein
                         organism = Heuchera sanguinea
SEQUENCE: 59
DGVKLCDVPS GTWSGHCGSS SKCSQQCKDR EHFAYGGACH YQFPSVKCFC KRQC                   54

SEQ ID NO: 60            moltype = AA   length = 49
FEATURE                  Location/Qualifiers
source                   1..49
                         mol_type = protein
                         organism = Clitoria ternatea
SEQUENCE: 60
NLCERASLTW TGNCGNTGHC DTQCRNWESA KHGACHKRGN WKCFCYFNC                         49

SEQ ID NO: 61            moltype = AA   length = 91
FEATURE                  Location/Qualifiers
source                   1..91
                         mol_type = protein
                         organism = Mus musculus
SEQUENCE: 61
MKKLVLLFAL VLLAFQVQAD SIQNTDEETK TEEQPGEKDQ AVSVSFGDPQ GSALQDAALG             60
WGRRCPQCPR CPSCPSCPRC PRCPRCKCNP K                                            91

SEQ ID NO: 62            moltype = AA   length = 40
FEATURE                  Location/Qualifiers
```

```
                                    -continued source                    1..40
                          mol_type = protein
                          organism = Bos taurus
SEQUENCE: 62
QGVRNFVTCR INRGFCVPIR CPGHRRQIGT CLGPQIKCCR                                40

SEQ ID NO: 63             moltype = AA   length = 40
FEATURE                   Location/Qualifiers
source                    1..40
                          mol_type = protein
                          organism = Bos taurus
SEQUENCE: 63
QGVRNFVTCR INRGFCVPIR CPGHRRQIGT CLGPRIKCCR                                40

SEQ ID NO: 64             moltype = AA   length = 42
FEATURE                   Location/Qualifiers
source                    1..42
                          mol_type = protein
                          organism = Bos taurus
SEQUENCE: 64
QGVRNHVTCR IYGGFCVPIR CPGRTRQIGT CFGRPVKCCR RW                             42

SEQ ID NO: 65             moltype = AA   length = 40
FEATURE                   Location/Qualifiers
source                    1..40
                          mol_type = protein
                          organism = Bos taurus
SEQUENCE: 65
QVVRNPQSCR WNMGVCIPIS CPGNMRQIGT CFGPRVPCCR                                40

SEQ ID NO: 66             moltype = AA   length = 41
FEATURE                   Location/Qualifiers
source                    1..41
                          mol_type = protein
                          organism = Bos taurus
SEQUENCE: 66
QRVRNPQSCR WNMGVCIPFL CRVGMRQIGT CFGPRVPCCR R                              41

SEQ ID NO: 67             moltype = AA   length = 42
FEATURE                   Location/Qualifiers
source                    1..42
                          mol_type = protein
                          organism = Bos taurus
SEQUENCE: 67
QGVRNHVTCR INRGFCVPIR CPGRTRQIGT CFGPRIKCCR SW                             42

SEQ ID NO: 68             moltype = AA   length = 40
FEATURE                   Location/Qualifiers
source                    1..40
                          mol_type = protein
                          organism = Bos taurus
SEQUENCE: 68
QGVRSYLSCW GNRGICLLNR CPGRMRQIGT CLAPRVKCCR                                40

SEQ ID NO: 69             moltype = AA   length = 42
FEATURE                   Location/Qualifiers
source                    1..42
                          mol_type = protein
                          organism = Bos taurus
SEQUENCE: 69
SGISGPLSCG RNGGVCIPIR CPVPMRQIGT CFGRPVKCCR SW                             42

SEQ ID NO: 70             moltype = AA   length = 38
FEATURE                   Location/Qualifiers
source                    1..38
                          mol_type = protein
                          organism = Bos taurus
SEQUENCE: 70
DFASCHTNGG ICLPNRCPGH MIQIGICFRP RVKCCRSW                                  38

SEQ ID NO: 71             moltype = AA   length = 74
FEATURE                   Location/Qualifiers
source                    1..74
                          mol_type = protein
                          organism = Zophobas atratus
SEQUENCE: 71
SLQGGAPNFP QPSQQNGGWQ VSPDLGRDDK GNTRGQIEIQ NKGKDHDFNA GWGKVIRGPN          60
KAKPTWHVGG TYRR                                                           74
```

```
SEQ ID NO: 72            moltype = AA  length = 67
FEATURE                  Location/Qualifiers
source                   1..67
                         mol_type = protein
                         organism = Homo sapiens
SEQUENCE: 72
MRIHYLLFAL LFLFLVPVPG HGGIINTLQK YYCRVRGGRC AVLSCLPKEE QIGKCSTRGR   60
KCCRRKK                                                             67

SEQ ID NO: 73            moltype = AA  length = 40
FEATURE                  Location/Qualifiers
source                   1..40
                         mol_type = protein
                         organism = Aedes aegypti
SEQUENCE: 73
ATCDLLSGFG VGDSACAAHC IARGNRGGYC NSKKVCVCRN                         40

SEQ ID NO: 74            moltype = AA  length = 35
FEATURE                  Location/Qualifiers
source                   1..35
                         mol_type = protein
                         organism = Mytilus edulis
SEQUENCE: 74
GFGCPNDYPC HRHCKSIPGR YGGYCGGXHR LRCTC                              35

SEQ ID NO: 75            moltype = AA  length = 40
FEATURE                  Location/Qualifiers
source                   1..40
                         mol_type = protein
                         organism = Sarcophaga peregrine
SEQUENCE: 75
ATCDLLSGIG VQHSACALHC VFRGNRGGYC TGKGICVCRN                         40

SEQ ID NO: 76            moltype = AA  length = 95
FEATURE                  Location/Qualifiers
source                   1..95
                         mol_type = protein
                         organism = Oryctolagus cuniculus
SEQUENCE: 76
MRTLALLAAI LLVALQAQAE HVSVSIDEVV DQQPPQAEDQ DVAIYVKEHE SSALEALGVK   60
AGVVCACRRA LCLPRERRAG FCRIRGRIHP LCCRR                              95

SEQ ID NO: 77            moltype = AA  length = 92
FEATURE                  Location/Qualifiers
source                   1..92
                         mol_type = protein
                         organism = Mus musculus
SEQUENCE: 77
MKPLVLLSAL VLLSFQVQAD PIQNTDEETK TEEQSGEEDQ AVSVSFGDRE GASLQEESLR   60
DLVCYCRTRG CKRRERMNGT CRKGHLMYTL CC                                 92

SEQ ID NO: 78            moltype = AA  length = 93
FEATURE                  Location/Qualifiers
source                   1..93
                         mol_type = protein
                         organism = Mus musculus
SEQUENCE: 78
MKTFVLLSAL VLLAFQVQAD PIHKTDEETN TEEQPGEEDQ AVSISFGGQE GSALHEELSK   60
KLICYCRIRG CKRRERVFGT CRNLFLTFVF CCS                                93

SEQ ID NO: 79            moltype = AA  length = 35
FEATURE                  Location/Qualifiers
source                   1..35
                         mol_type = protein
                         organism = Mus musculus
SEQUENCE: 79
LRDLVCYCRA RGCKGRERMN GTCRKGHLLY MLCCR                              35

SEQ ID NO: 80            moltype = AA  length = 43
FEATURE                  Location/Qualifiers
source                   1..43
                         mol_type = protein
                         organism = Pyrrhocoris apterus
SEQUENCE: 80
ATCDILSFQS QWVTPNHAGC ALHCVIKGYK GGQCKITVCH CRR                     43

SEQ ID NO: 81            moltype = AA  length = 32
FEATURE                  Location/Qualifiers
source                   1..32
```

```
                          mol_type = protein
                          organism = Rattus norvegicus
SEQUENCE: 81
VTCYCRSTRC GFRERLSGAC GYRGRIYRLC CR                                32

SEQ ID NO: 82             moltype = AA   length = 31
FEATURE                   Location/Qualifiers
source                    1..31
                          mol_type = protein
                          organism = Rattus norvegicus
SEQUENCE: 82
VTCSCRTSSC RFGERLSGAC RLNGRIYRLC C                                 31

SEQ ID NO: 83             moltype = AA   length = 34
FEATURE                   Location/Qualifiers
source                    1..34
                          mol_type = protein
                          organism = Oryctolagus cuniculus
SEQUENCE: 83
GICACRRRFC LNFEQFSGYC RVNGARYVRC CSRR                              34

SEQ ID NO: 84             moltype = AA   length = 64
FEATURE                   Location/Qualifiers
source                    1..64
                          mol_type = protein
                          organism = Pan troglodytes
SEQUENCE: 84
MRVLYLLFSF LFIFLMPLPG VFGGISDPVT CLKSGAICHP VFCPRRYKQI GTCGLPGTKC  60
CKKP                                                              64

SEQ ID NO: 85             moltype = AA   length = 64
FEATURE                   Location/Qualifiers
source                    1..64
                          mol_type = protein
                          organism = Homo sapiens
SEQUENCE: 85
MRVLYLLFSF LFIFLMPLPG VFGGIGDPVT CLKSGAICHP VFCPRRYKQI GTCGLPGTKC  60
CKKP                                                              64

SEQ ID NO: 86             moltype = AA   length = 68
FEATURE                   Location/Qualifiers
source                    1..68
                          mol_type = protein
                          organism = Homo sapiens
SEQUENCE: 86
MRTSYLLLFT LCLLLSEMAS GGNFLTGLGH RSDHYNCVSS GGQCLYSACP IFTKIQGTCY  60
RGKAKCCK                                                          68

SEQ ID NO: 87             moltype = AA   length = 64
FEATURE                   Location/Qualifiers
source                    1..64
                          mol_type = protein
                          organism = Capra hircus
SEQUENCE: 87
MRLHHLLLVL FFLVLSAGSG FTQGIRSRRS CHRNKGVCAL TRCPRNMRQI GTCFGPPVKC  60
CRKK                                                              64

SEQ ID NO: 88             moltype = AA   length = 64
FEATURE                   Location/Qualifiers
source                    1..64
                          mol_type = protein
                          organism = Capra hircus
SEQUENCE: 88
MRLHHLLLAL FFLVLSAGSG FTQGIINHRS CYRNKGVCAP ARCPRNMRQI GTCHGPPVKC  60
CRKK                                                              64

SEQ ID NO: 89             moltype = AA   length = 96
FEATURE                   Location/Qualifiers
source                    1..96
                          mol_type = protein
                          organism = Macaca mulatta
SEQUENCE: 89
MRTLVILAAI LLVALQAQAE PLQARTDEAT AAQEQIPTDN PEVVVSLAWD ESLAPKDSVP  60
GLRKNMACYC RIPACLAGER RYGTCFYRRR VWAFCC                           96

SEQ ID NO: 90             moltype = AA   length = 96
FEATURE                   Location/Qualifiers
source                    1..96
                          mol_type = protein
```

```
                        organism = Macaca mulatta
SEQUENCE: 90
MRTLVILAAI LLVALQAQAE PLQARTDEAT AAQEQIPTDN PEVVVSLAWD ESLAPKDSVP    60
GLRKNMACYC RIPACLAGER RYGTCFYLGR VWAFCC                              96

SEQ ID NO: 91           moltype = AA  length = 33
FEATURE                 Location/Qualifiers
source                  1..33
                        mol_type = protein
                        organism = Mesocricetus auratus
SEQUENCE: 91
VTCFCRRRGC ASRERHIGYC RFGNTIYRLC CRR                                 33

SEQ ID NO: 92           moltype = AA  length = 31
FEATURE                 Location/Qualifiers
source                  1..31
                        mol_type = protein
                        organism = Mesocricetus auratus
SEQUENCE: 92
CFCKRPVCDS GETQIGYCRL GNTFYRLCCR Q                                   31

SEQ ID NO: 93           moltype = AA  length = 39
FEATURE                 Location/Qualifiers
source                  1..39
                        mol_type = protein
                        organism = Gallus gallus
SEQUENCE: 93
GRKSDCFRKN GFCAFLKCPY LTLISGKCSR FHLCCKRIW                           39

SEQ ID NO: 94           moltype = AA  length = 43
FEATURE                 Location/Qualifiers
source                  1..43
                        mol_type = protein
                        organism = Allomyrina dichotoma
SEQUENCE: 94
VTCDLLSFEA KGFAANHSLC AAHCLAIGRR GGSCERGVCI CRR                      43

SEQ ID NO: 95           moltype = AA  length = 31
FEATURE                 Location/Qualifiers
source                  1..31
                        mol_type = protein
                        organism = Cavia porcellus
SEQUENCE: 95
RRCICTTRTC RFPYRRLGTC IFQNRVYTFC C                                   31
```

METHODS AND COMPOSITIONS FOR WOUND HEALING

CROSS REFERENCE TO RELATED APPLICATIONS

The present application is a continuation of U.S. patent application Ser. No. 15/663,172, filed Jul. 28, 2017, allowed as U.S. Pat. No. 11,554,194, which claims the priority benefit of U.S. Provisional Patent Application 62/368,646, filed Jul. 29, 2016, which are incorporated by reference in their entireties.

SEQUENCE LISTING

The text of the computer readable sequence listing filed herewith, titled "34937_303_SequenceListing", created Jan. 17, 2023, having a file size of 86,000 bytes, is hereby incorporated by reference in its entirety.

FIELD OF THE INVENTION

The present invention relates to large scale manufacture of nanoscale microsheets for use in applications such as wound healing or modification of a biological or medical surface.

BACKGROUND OF THE INVENTION

Molecularly thin polymeric sheets containing a bioactive agent have been shown to be useful in promoting wound healing and preventing bacterial infection at the site of a wound. See, e.g., co-pending U.S. Pat. Publ. 2015/0283287, incorporated herein by reference in its entirety. However, the large scale manufacture of such thin polymeric sheets has not been previously described. The previously described methods rely primarily on batch productions which are small scale production techniques that are slow and inefficient in use of reagents as well as being limited to production of microsheets with relatively small surface areas.

What is needed in the art are large-scale methods for producing nano- to microscale polymeric sheets in an efficient manner.

SUMMARY OF THE INVENTION

The present invention relates to large scale manufacture of nanoscale microsheets for use in applications such as wound healing or modification of a biological or medical surface.

In some embodiments, the present invention provides an article comprising: a flexible substrate comprising a low surface energy surface and having a total surface area of greater than 0.52 square meters; and a nanoscale polymer layer adjacent to and in contact with the low surface energy surface, the nanoscale polymer layer having a thickness of from 0.5 nm to 10000 nm thick.

In some embodiments, the nanoscale polymer layer is a polymer multilayer. In some embodiments, the polymer multilayer comprises alternating layers of at least one positively charged polyelectrolyte and at least one negatively charged polyelectrolyte. In some embodiments, the at least one positively charged polyelectrolyte is selected form the group consisting of poly(allylamine hydrochloride) (PAH), polyl-lysine (PLL), poly(ethylene imine) (PEI), poly(histidine), poly(N,N-dimethyl aminoacrylate), poly(N,N,N-trimethylaminoacrylate chloride), poly(methyacrylamidopropyltrimethyl ammonium chloride), and natural or synthetic polysaccharides such as chitosan. In some embodiments, the at least one negatively charged polyelectrolyte is selected from the group consisting of poly(acrylic acid) (PAA), poly(styrenesulfonate) (PSS), alginate, hyaluronic acid, heparin, heparan sulfate, chondroitin sulfate, dextran sulfate, poly(methacrylic acid), oxidized cellulose, carboxymethyl cellulose, polyaspartic acid, and polyglutamic acid. In some embodiments, the at least one positively charged polyelectrolyte and the at least one negatively charged polyelectrolyte are synthetic polyelectrolytes.

In some embodiments, the nanoscale polymer layer is formed by applying the at least one positively charged polyelectrolyte and at least one negatively charged polyelectrolyte by a method selected from the group consisting of spray coating, dip coating, immersion coating, spin coating, slot die coating, inkjet coating, anilox coating, screen coating, offset lithography printing, flexographic coating, gravure coating, rotogravure coating, reverse roll coating, metering (Meyer) rod coating, blade coating, knife over roll coating, air knife coating, curtain coating, melt extrusion coating, solvent casting and any combinations thereof.

In some embodiments, the flexible substrate has a surface area of greater than 0.65 square meters.

In some embodiments, the articles further comprise a bioactive agent incorporated into the nanoscale polymer layer. In some embodiments, the bioactive agent is interspersed within the three dimensional structure of the nanoscale polymer layer or interspersed within the layers of the polymer multilayer. In some embodiments, the bioactive agent is selected from the group consisting of an antimicrobial agent, an antibiofilm agent, a growth factor, a hemostatic agent, a bioactive peptide, a bioactive polypeptide, an analgesic, a local anesthetic, an opioid, an opioid antagonist or mixed agonist/antagonist, an anticoagulant, anti-inflammatory agent, and a drug molecule or a drug compound. In some embodiments, the antimicrobial agent is selected from the groups consisting of small molecule antimicrobial agents, charged small molecule antimicrobial agents, antimicrobial polypeptides, metallic particles, and metal ion antimicrobial agents. In some embodiments, the metal ion antimicrobial agent is a metal ion, metal ion salt, or metal ion nanoparticle. In some embodiments, the metal ion antimicrobial agent is a silver ion, silver salt, or silver nanoparticle. In some embodiments, the small molecule antimicrobial agent is selected from the group consisting of silver, chlorhexidine, antibiotics, polyhexamethylene biguanide (PHMB), iodine, cadexomer iodine, povidone iodine (PVI), hydrogen peroxide, and vinegar (acetic acid). In some embodiments, the antibiofilm agent is selected from the group consisting of small molecule antibiofilm agents, charged small molecule antibiofilm agents, antibiofilm polypeptides, antibiofilm enzymes, metallic particles, and metal ion antibiofilm agents. In some embodiments, the metal ion antibiofilm agent is a metal ion, metal ion salt, or metal ion nanoparticle. In some embodiments, the metal ion antibiofilm agent is a gallium ion, gallium ion salt, gallium ion nanoparticle, gallium alloy, or an alloy of gallium and silver. In some embodiments, the antibiofilm enzyme is Dispersin B. In some embodiments, the local anaesthetic is selected from the group consisting of bupivacaine, lidocaine, articaine, prilocaine, and mepivacaine. In some embodiments, the opioid is selected from the group consisting of codeine, fentanyl, hydrocodone, hydrocodone and acetaminophen, hydromorphone, meperidine, morphine, oxycodone, oxycodone and acetaminophen, oxycodone and naloxone. In some embodiments, the opioid antagonist or mixed agonist/antagonist is selected from the group consisting of naloxone, diprenorphine, naltrexone, buprenorphine, bupremorphine/naloxone.

In some embodiments, the articles further comprise a second polymer layer adjacent to and in contact with the nanoscale polymer layer so that the nanoscale polymer layer is between the low surface energy surface of the substrate and the second polymer layer. In some embodiments, the second polymer layer decreases the release of bioactive agent from nanoscale layer by 1 to 1000 times, 1 to 100 times, 10 to 1000 times, 20 to 1000 times, 50 to 1000 times, 100 to 1000 times, 10 to 500 times, 50 to 500 times, 10 to 200 times or 20 to 200 times.

In some embodiments, the second polymer layer is a sacrificial polymer layer. In some embodiments, the sacrificial polymer layer is dissolvable or biodegradable. In some embodiments, the sacrificial polymer layer comprises a water soluble polymer. In some embodiments, the water soluble polymer is removable by renal filtration. In some embodiments, the water soluble polymer has a molecular weight of less than 23 kDa. In some embodiments, the sacrificial polymer layer comprising a water soluble polymer dissolves when exposed to moisture on a surface so that the bioactive nanoscale polymer layer is deposited on the surface. In some embodiments, the sacrificial polymer layer comprises polyvinyl alcohol (PVA). In some embodiments, the second polymer layer comprises polyacrylic acid (PAA), polyvinylpyrrolidone (PVP), carboxymethyl cellulose (CMC), hydroxypropyl cellulose, hydroxypropyl methylcellulose, methylcellulose, ethylcellulose, hydroxyethyl cellulose (HEC), alginates, polyvinylacetate (PVAc), polylactic acid (PLA), polylactic-co-glycolic acid (PLGA), polyglycolic acid, or polyanhydrides. In some embodiments, the polymers in the second polymer layer are ionically, physically or chemically cross-linked. In some embodiments, the sacrificial layer comprises one or more additive selected from the group consisting of surfactants, emulsifiers, wetting agents, rheology modifiers, plasticizers, emollients, humectants, disintegrants, lubricants, binders, compatibilizing agents, antistatic agents, and fillers.

In some embodiments, the second polymer layer is a non-sacrificial polymer layer. In some embodiments, the non-sacrificial polymer layer comprises collagen, a hydrogel, a hydrocolloid, polyurethane, or silicone. In some embodiments, the second polymer layer in combination with the nanoscale polymer layer is releasable from the low surface energy surface of the substrate.

In some embodiments, the second polymer layer comprises a bioactive agent. In some embodiments, the bioactive agent is selected from the group consisting of an antimicrobial agent, an antibiofilm agent, a growth factor, a hemostatic agent, a bioactive peptide, a bioactive polypeptide, an analgesic, a local anesthetic, an opioid, an opioid agonist, an opioid antagonist or mixed agonist/antagonist, an anticoagulant, anti-inflammatory agent, and a drug molecule or a drug compound. In some embodiments, the antimicrobial agent is selected from the group consisting of small molecule antimicrobial agents, charged small molecule antimicrobial agents, antimicrobial polypeptides, metallic particles, and metal ion antimicrobial agents. In some embodiments, the metal ion antimicrobial agent is a metal ion, metal ion salt, or metal ion nanoparticle. In some embodiments, the metal ion antimicrobial agent is a silver ion, silver salt, or silver nanoparticle. In some embodiments, the small molecule antimicrobial agent is selected from the group consisting of silver, chlorhexidine, antibiotics, polyhexamethylene biguanide (PHMB), iodine, cadexomer iodine, povidone iodine (PVI), hydrogen peroxide, and vinegar (acetic acid). In some embodiments, the antibiofilm agent is selected from the group consisting of small molecule antibiofilm agents, charged small molecule antibiofilm agents, antibiofilm polypeptides, antibiofilm enzymes, metallic particles, and metal ion antibiofilm agents. In some embodiments, the metal ion antibiofilm agent is a metal ion, metal ion salt, or metal ion nanoparticle. In some embodiments, the metal ion antibiofilm agent is a gallium ion, gallium ion salt, gallium ion nanoparticle, gallium alloy, or an alloy of gallium and silver. In some embodiments, the antibiofilm enzyme is Dispersin B. In some embodiments, the local anaesthetic is selected from the group consisting of bupivacaine, lidocaine, articaine, prilocaine, and mepivacaine. In some embodiments, the opioid is selected from the group consisting of codeine, fentanyl, hydrocodone, hydrocodone and acetaminophen, hydromorphone, meperidine, morphine, oxycodone, oxycodone and acetaminophen, oxycodone and naloxone. In some embodiments, the opioid antagonist or mixed agonist/antagonist is selected from the group consisting of naloxone, diprenorphine, naltrexone, buprenorphine, bupremorphine/naloxone.

In some embodiments, the second polymer layer is from about 0.1 µm thick to about 100 µm thick, from about 0.1 µm thick to about 50 µm thick, from about 1 µm thick to about 20 µm thick, or from about 1 µm thick to about 10 µm thick. In some embodiments, the bioactive agent at a concentration of approximately 0.01 to 100 µg/cm$^2$ in nanoscale polymer layer. In some embodiments, the bioactive agent is provided in nanoscale polymer layer in an amount so that the bioactive agent is released at a rate of about 0.01 to 100 µg/cm$^2$ per day. In some embodiments, the bioactive agent is provided in nanoscale polymer layer in an amount so that the bioactive agent is released at a rate of about 0.01 to 100 µg/cm$^2$ per day for up to 5, 10, 20, 25, or 30 days. In some embodiments, the bioactive agent is included at a concentration of approximately 0.01 µg/cm$^2$ to 10 mg/cm$^2$ in the second polymer layer. In some embodiments, the bioactive agent is provided in the second polymer layer in an amount so that the bioactive agent is released at a rate of about 0.01 µg/cm$^2$ to 10 mg/cm$^2$ per day. In some embodiments, the bioactive agent is provided in the second polymer layer in an amount so that the bioactive agent is released at a rate of about 0.01 µg/cm$^2$ to 10 mg/cm$^2$ per day for up to 5, 10, 20, 25, or 30 days. In some embodiments, the second polymer layer has a uniform thickness with a variation of less than 500, 400, 300, 200, 100, 50, 20 or 10% of the average thickness when measured in cross section.

In some embodiments, the articles further comprise a second or more bioactive agent(s).

In some embodiments, the low surface energy surface on the flexible substrate has a surface energy of from 10 to 100 mJ/cm$^2$ (e.g., 10 to 60 mJ/cm$^2$).

In some embodiments, the flexible substrate is a flexible polymeric sheet of low surface energy or the low surface energy surface is provided by a release coating coated on the flexible polymer. In some embodiments, the release coating is a silicone release coating, a polydimethyl siloxane (PDMS) coating, a fluorocarbon coating, a polyacrylate coating, a polystyrene coating, a polystyreneacrylic coating, a chromium sterate complex coating, or a polyolefin coating. In some embodiments, the flexible polymeric sheet comprises a polymer film selected from the group consisting of a polyester film, a polyethylene terephthalate (PET) film, a biaxially oriented PET film, a polycarbonate, a polyethylene (including high density polyethylene, medium density polyethylene, low density polyethylene, linear low density polyethylene) film, a polyvinyl chloride film, a polyvinylidene chloride film, a polyvinylidene fluoride film, a nylon film, a polystyrene film, an acetate film, a polyurethane film, an ethylene vinyl acetate copolymer film, a cast polypropylene film, an uniaxially oriented polypropylene film and a biaxially oriented polypropylene film.

In some embodiments, the present invention provides processes for manufacture of an article comprising: a) providing a flexible substrate comprising a low surface energy surface and having a surface area of greater than 0.52 square meters; b) depositing a nanoscale polymer layer from about 0.5 nm to 10000 nm thick on the low surface energy surface; and c) introducing a bioactive agent into the nanoscale polymer layer to provide a bioactive nanoscale polymer layer to provide said article. In some embodiments, the surface area of flexible substrate comprising a low surface energy surface is greater than 0.65 square meters.

In some embodiments, the depositing occurs via a roll to roll coating process. In some embodiments, the roll to roll coating process comprises transferring the flexible substrate from a first roll to at least a second roll and coating the low surface energy surface of the flexible substrate with the nanoscale polymer layer while the flexible substrate is being transferred between the first roll and the second roll. In some embodiments, the nanoscale polymer layer is coated on the low surface energy surface of the flexible substrate by a coating or printing method selected from the group consisting of spray coating, dip coating, immersion coating, spin coating, slot die coating, inkjet coating, anilox coating, screen coating, offset lithography printing, flexographic coating, gravure coating, rotogravure coating, reverse roll coating, metering (Meyer) rod coating, blade coating, knife over roll coating, air knife coating, curtain coating, melt extrusion coating, solvent casting and any combinations thereof.

In some embodiments, the nanoscale polymer layer is a polymer multilayer. In some embodiments, the nanoscale polymer layer is formed by alternating layers of at least one positively charged polyelectrolyte and at least one negatively charged polyelectrolyte. In some embodiments, the at least one positively charged polyelectrolyte is selected form the group consisting of poly(allylamine hydrochloride) (PAH), polyl-lysine (PLL), poly(ethylene imine) (PEI), poly (histidine), poly(N,N-dimethyl aminoacrylate), poly(N,N, N-trimethylaminoacrylate chloride), poly(methyacrylamidopropyltrimethyl ammonium chloride), and natural or synthetic polysaccharides such as chitosan. In some embodiments, the at least one negatively charged polyelectrolyte is selected from the group consisting of poly(acrylic acid) (PAA), poly(styrenesulfonate) (PSS), alginate, hyaluronic acid, heparin, heparan sulfate, chondroitin sulfate, dextran sulfate, poly(methacrylic acid), oxidized cellulose, carboxymethyl cellulose, polyaspartic acid, and polyglutamic acid. In some embodiments, the at least one positively charged polyelectrolyte and the at least one negatively charged polyelectrolyte are synthetic polyelectrolytes.

In some embodiments, the molecular weight of the polyelectrolyte is from 1-10000 kDa, 100 to 10000 kDa, 500 to 10000 kDa, 1000 to 10000 kDa, 50 to 500 kDa or 500 to 5000 kDa. In some embodiments, the polyelectrolyte has multimodal molecular weight distribution in the range 1 to 10000 kDa, 100 to 10000 kDa, 500 to 10000 kDa, 1000 to 10000 kDa, 50 to 500 kDa or 500 to 5000 kDa or is a mixture of multiple polymers of unimodal or multimodal molecular weight distribution in the range 1-10000 kDa, 100 to 10000 kDa, 500 to 10000 kDa, 1000 to 10000 kDa, 50 to 500 kDa or 500 to 5000 kDa. In some embodiments, the concentration of polyelectrolyte in its aqueous solution is 1 to 10000 mM, 10 to 10000 mM, 100 to 10000 mM, 10 to 1000 mMM, 10 to 500 mM, 10 to 50 mM, 1 to 50 mM, or 1 to 100 mM based on polymer repeat unit. In some embodiments, the pH of aqueous polyelectrolyte solution is adjusted so that the polymer is at least 0.01% charged. In some embodiments, the concentration of inorganic or organic salts is from 1 to 10000 mM, 10 to 10000 mM, 100 to 10000 mM, 10 to 1000 mMM, 10 to 500 mM, 10 to 50 mM, 1 to 50 mM, or 1 to 100 mM in the aqueous polyelectrolyte solution.

In some embodiments, the residence time of the polymer formulation on the low surface energy surface of the flexible substrate during the coating of nanoscale polymer layer is from 1 to 600 seconds, 50 to 600 seconds, 100 to 600 seconds, or 200 to 600 seconds, prior to rinsing.

In some embodiments, the processes further comprise incorporating a bioactive agent into the nanoscale polymer layer. In some embodiments, the bioactive agent is incorporated into the nanoscale polymer layer so that the bioactive agent is interspersed within the three dimensional structure of the nanoscale polymer layer. In some embodiments, the bioactive agent is incorporated into the nanoscale polymer multilayer so that the bioactive agent is interspersed within the layers of the polymer multilayer.

In some embodiments, the bioactive agent is selected from the group consisting of an antimicrobial agent, an antibiofilm agent, a growth factor, a hemostatic agent, a bioactive peptide, a bioactive polypeptide, an analgesic, a local anesthetic, opioid, opioid agonist, opioid antagonist or mixed agonist/antagonist, an anticoagulant, anti-inflammatory agent, and a drug molecule or a drug compound. In some embodiments, the antimicrobial agent is selected from the groups consisting of small molecule antimicrobial agents, charged small molecule antimicrobial agents, antimicrobial polypeptides, metallic particles, and metal ion antimicrobial agents. In some embodiments, the metal ion antimicrobial agent is a metal ion, metal ion salt, or metal ion nanoparticle. In some embodiments, the metal ion nanoparticle is a silver nanoparticle. In some embodiments, the small molecule antimicrobial agent is selected from the group consisting of silver, chlorhexidine, antibiotics, polyhexamethylene biguanide (PHMB), iodine, cadexomer iodine, povidone iodine (PVI), hydrogen peroxide, and vinegar (acetic acid). In some embodiments, the antibiofilm agent is selected from the group consisting of small molecule antibiofilm agents, charged small molecule antibiofilm agents, antibiofilm polypeptides, antibiofilm enzymes, metallic particles, and metal ion antibiofilm agents. In some embodiments, the metal ion antibiofilm agent is a metal ion, metal ion salt, or metal ion nanoparticle. In some embodiments, the metal ion antibiofilm agent is a gallium ion, gallium ion salt, gallium ion nanoparticle, gallium alloy, or an alloy of gallium and silver. In some embodiments, the antibiofilm enzyme is Dispersin B. In some embodiments, the analgesic is selected from the group consisting of bupivacaine, lidocaine, articaine, prilocaine, and mepivacaine. In some embodiments, the opioid is selected from the group consisting of codeine, fentanyl, hydrocodone, hydrocodone and acetaminophen, hydromorphone, meperidine, morphine, oxycodone, oxycodone and acetaminophen, oxycodone and naloxone. In some embodiments, the opioid antagonist or mixed agonist/antagonist is selected from the group consisting of naloxone, diprenorphine, naltrexone, buprenorphine, bupremorphine/naloxone.

In some embodiments, the bioactive agent is introduced into the nanoscale polymer layer during the formation of the nanoscale polymer layer. In some embodiments, the bioactive agent is introduced into the nanoscale polymer layer after formation of the nanoscale polymer layer.

In some embodiments, the introducing the bioactive agent into the nanoscale polymer layer to provide a bioactive nanoscale polymer layer comprises introducing silver ions into the nanoscale polymer multilayer and reducing the silver ions in situ to provide silver nanoparticles. In some embodiments, the nanoscale film is doped with silver ions by immersion in silver nitrate solution of concentration of from 0.1-10000 mM, 1 to 10000 mM, 10 to 10000 mM, 100 to 10000 mM, 10 to 1000 mMM, 10 to 500 mM, 10 to 50 mM, 1 to 50 mM, or 1 to 100 mM for from 1 to 3600 seconds, 100 to 3600 seconds, 200 to 3600 seconds, 400 to 3600 seconds or 600 to 3600 seconds. In some embodiments, silver ion in the nanoscale film is reduced into silver nanoparticles by immersing nanoscale film in a solution of a reducing agent solution of concentration of from 0.1 to 10000 mM, 1 to 10000 mM, 10 to 10000 mM, 100 to 10000 mM, 10 to 1000 mMM, 10 to 500 mM, 10 to 50 mM, 1 to 50 mM, or 1 to 100 mM for from 1 to 3600 seconds, 100 to 3600 seconds, 200 to 3600 seconds, 400 to 3600 seconds or 600 to 3600 seconds. In some embodiments, the reducing agent is sodium borohydride.

In some embodiments, the incorporating the bioactive agent into the nanoscale polymer layer to provide a bioactive nanoscale polymer layer comprises introducing a charged small molecule antimicrobial agent in between polyelectrolyte layers having a different charge.

In some embodiments, the processes further comprise 1 to 20 repetitions of the incorporating step.

In some embodiments, the processes further comprise controlling the amount of the bioactive agent in the nanoscale polymer matrix microsheet by controlling the number of nanoscale polymer layers, by controlling the pH of forming the nanoscale polymer layer, and/or by controlling the number of introducing cycles. In some embodiments, the processes further comprise controlling the amount of the bioactive agent in the nanoscale polymer matrix microsheet by controlling the concentration of bioactive solution and/or by controlling the residence time of nanoscale polymer layer in bioactive solution.

In some embodiments, the processes further comprising forming or depositing a second polymer layer on the nanoscale polymer-layer so that the nanoscale polymer layer is between the low surface energy surface of the flexible polymer substrate and the second polymer layer. In some embodiments, the second polymer layer slows the release of bioactive agent from nanoscale layer by 1 to 1000 times, 1 to 100 times, 10 to 1000 times, 20 to 1000 times, 50 to 1000 times, 100 to 1000 times, 10 to 500 times, 50 to 500 times, 10 to 200 times or 20 to 200 times.

In some embodiments, the second polymer layer is a sacrificial polymer layer. In some embodiments, the sacrificial polymer layer is dissolvable or biodegradable. In some embodiments, the sacrificial polymer layer comprises a water soluble polymer. In some embodiments, the water soluble polymer is polyvinyl alcohol (PVA). In some embodiments, the water soluble polymer has a molecular weight of less than 23 kDa. In some embodiments, the water soluble polymer is removable by renal filtration. In some embodiments, the sacrificial polymer layer comprising a water soluble polymer dissolves when exposed to moisture on a surface so that the bioactive nanoscale polymer layer is deposited on the surface. In some embodiments, the second polymer layer comprises polyacrylic acid (PAA), polyvinylpyrrolidone (PVP), carboxymethyl cellulose (CMC), hydroxypropyl cellulose, hydroxypropyl methylcellulose, methylcellulose, ethylcellulose, hydroxyethyl cellulose (HEC), alginates, polyvinylacetate (PVAc), polylactic acid (PLA), polylactic-co-glycolic acid (PLGA), polyglycolic acid, or polyanhydrides.

In some embodiments, the polymers in the second polymer layer are ionically, physically or chemically cross-linked.

In some embodiments, the second polymer layer comprises one or more additives selected from the group consisting of surfactants, emulsifiers, wetting agents, rheology modifiers, plasticizers, emollients, humectants, disintegrants, lubricants, binders, compatibilizing agents, antistatic agents, and fillers.

In some embodiments, the second polymer layer is a non-sacrificial polymer layer. In some embodiments, the non-sacrificial polymer layer comprises collagen, a hydrogel, a hydrocolloid, polyurethane or silicone.

In some embodiments, the second polymer layer is from about 0.1 µm thick to about 100 µm thick, from about 0.1 µm thick to about 50 µm thick, from about 1 µm thick to about 20 µm thick, or from about 1 µm thick to about 10 µm thick.

In some embodiments, the second polymer layer in combination with the nanoscale polymer layer is releasable from the low surface energy surface of the substrate to provide a freestanding microsheet.

In some embodiments, the processes further comprise introducing a bioactive agent into the second polymer layer. In some embodiments, the bioactive agent is selected from the group consisting of an antimicrobial agent, an antibiofilm agent, a growth factor, a hemostatic agent, a bioactive peptide, a bioactive polypeptide, an analgesic, an anticoagulant, an anti-inflammatory agent, and a drug molecule or a drug compound. In some embodiments, the antimicrobial agent is selected from the group consisting of small molecule antimicrobial agents, charged small molecule antimicrobial agents, antimicrobial polypeptides, metallic particles, and metal ion antimicrobial agents. In some embodiments, the metal ion antimicrobial agent is a metal ion, metal ion salt, or metal ion nanoparticle. In some embodiments, the metal ion nanoparticle is a silver nanoparticle. In some embodiments, the small molecule antimicrobial agent is selected from the group consisting of silver, chlorhexidine, antibiotics, polyhexamethylene biguanide (PHMB), iodine, cadexomer iodine, povidone iodine (PVI), hydrogen peroxide, and vinegar (acetic acid). In some embodiments, the antibiofilm agent is selected from the group consisting of small molecule antibiofilm agents, charged small molecule antibiofilm agents, antibiofilm polypeptides, antibiofilm enzymes, metallic particles, and metal ion antibiofilm agents. In some embodiments, the metal ion antibiofilm agent is a metal ion, metal ion salt, or metal ion nanoparticle. In some embodiments, the metal ion antibiofilm agent is a gallium ion, gallium ion salt, gallium ion nanoparticle, gallium alloy, or an alloy of gallium and silver. In some embodiments, the antibiofilm enzyme is Dispersin B. In some embodiments, the local anaesthetic is selected from the group consisting of bupivacaine, lidocaine, articaine, prilocaine, and mepivacaine. In some embodiments, the opioid is selected from the group consisting of codeine, fentanyl, hydrocodone, hydrocodone and acetaminophen, hydromorphone, meperidine, morphine, oxycodone, oxycodone and acetaminophen, oxycodone and naloxone. In some embodiments, the opioid antagonist or mixed agonist/antagonist is selected from the group consisting of naloxone, diprenorphine, naltrexone, buprenorphine, bupremorphine/naloxone.

In some embodiments, the bioactive agent is loaded at a concentration of approximately 0.01 to 100 µg/cm$^2$ in the nanoscale polymer layer. In some embodiments, the bioactive agent is provided in nanoscale polymer layer in an amount so that the bioactive agent is released at a rate of about 0.01 to 100 µg/cm$^2$ per day. In some embodiments, the bioactive agent is provided in nanoscale polymer layer in an amount so that the bioactive agent is released at a rate of about 0.01 to 100 µg/cm$^2$ per day for up to 5, 10, 20, 25, or 30 days. In some embodiments, the bioactive agent is provided in the second polymer layer at a concentration of approximately 0.01 µg/cm$^2$ to 10 mg/cm$^2$. In some embodiments, the bioactive agent is provided in the second polymer layer in an amount so that the bioactive agent is released at a rate of about 0.01 µg/cm$^2$ to 10 mg/cm$^2$ per day. In some embodiments, the bioactive agent is provided in the second polymer layer in an amount so that the bioactive agent is released at a rate of about 0.01 µg/cm$^2$ to 10 mg/cm$^2$ per day for up to 5, 10, 20, 25, or 30 days.

In some embodiments, the processes further comprise including a second or more bioactive agent(s) in the combined nanoscale polymer layer and the second polymer layer.

In some embodiments, low surface energy surface on the flexible substrate has a surface energy of from 10 to 100 mJ/cm$^2$. In some embodiments, the flexible substrate is a flexible polymeric sheet of low surface energy or the low surface energy surface is provided by a release coating coated on the flexible polymer. In some embodiments, the release coating is a silicone release coating, a polydimethyl siloxane (PDMS) coating, a fluorocarbon coating, a polyacrylate coating, a polystyrene coating, a polystyreneacrylic coating, a chromium sterate complex coating, or a polyolefin coating. In some embodiments, the flexible polymeric sheet comprises a polymer film selected from the group consisting of a polyester film, a polyethylene terephthalate (PET) film, a biaxially oriented PET film, a polycarbonate, a polyethylene (including high density polyethylene, medium density polyethylene, low density polyethylene, linear low density polyethylene) film, a polyvinyl chloride film, a polyvinylidene chloride film, a polyvinylidene fluoride film, a nylon film, a polystyrene film, an acetate film, a polyurethane film, an ethylene vinyl acetate copolymer film, a cast polypropylene film, an uniaxially oriented polypropylene film and a biaxially oriented polypropylene film.

In some embodiments, the processes further comprise peeling the nanoscale polymer layer in association with the second polymer layer from the low surface energy surface of the substrate to provide a free standing microsheet. In some embodiments, the processes further comprise cutting the substrate having a nanoscale polymer layer deposited thereon to a desired shape and size and peeling the nanoscale polymer layer in association with the second polymer layer from the low surface energy surface of the substrate. In some embodiments, the processes further comprise peeling the nanoscale polymer layer in association with the second polymer layer from the low surface energy surface of the substrate and cutting the nanoscale polymer layer in association with the second polymer layer to a desired shape and size.

It will be understood that where ranges are provided in the summary provided above, the present invention includes subranges that fall within the stated ranges.

Definitions

To facilitate an understanding of the invention set forth in the disclosure that follows, a number of terms are defined below.

The term "wound" refers broadly to injuries to the skin and subcutaneous tissue initiated in different ways (e.g., pressure sores from extended bed rest and wounds induced by trauma) and with varying characteristics. The methods and compositions described herein are useful for treatment of all types of wounds, including wounds to internal and external tissues, and wounds induced during medical procedures (e.g., surgical procedures) (e.g., abdominal surgery, hernia surgery, gastrointestinal surgery, bariatric surgery, reconstruction surgery, dural membrane surgery, etc.). Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum).

The term "partial thickness wound" refers to wounds that encompass Grades I-III; examples of partial thickness wounds include burn wounds, pressure sores, venous stasis ulcers, and diabetic ulcers. The term "deep wound" is meant to include both Grade III and Grade IV wounds. The present invention contemplates treating all wound types, including deep wounds and chronic wounds.

The term "chronic wound" refers to a wound that has not healed within 30 days.

The phrases "promote wound healing," "enhance wound healing," and the like refer to either the induction of the formation of granulation tissue of wound contraction and/or the induction of epithelialization (i.e., the generation of new cells in the epithelium). Wound healing is conveniently measured by decreasing wound area.

The term "bioactive agent" refers to known or potential chemical compounds that induce a desired pharmacological, physiological effect useful in the treatment and healing of a wound, wherein the effect may be prophylactic or therapeutic. The terms also encompass pharmaceutically acceptable, pharmacologically active derivatives of those active agents specifically mentioned herein, including, but not limited to, trophic factors, extracellular matrices, enzymes, enzyme inhibitors, defensins, polypeptides, anti-infective agents (including but not limited to ionic silver, elemental silver, and silver nanoparticles), buffering agents, vitamins and minerals, analgesics, anticoagulants, coagulation factors, anti-inflammatory agents, vasoconstrictors, vasodilators, diuretics, and anti-cancer agents.

The term "polymer multilayer" refers to the composition formed by sequential and repeated application of polymer(s) to form a multilayered structure. For example, polyelectrolyte multilayers are polymer multilayers are formed by the alternating addition of anionic and cationic polyelectrolytes to a wound or support. The term "polymer multilayer" also refers to the composition formed by sequential and repeated application of polymer(s) to a wound or to a solid support. In addition, the term "polymer layer" can refer to a single layer composed of polymer molecules, such as anionic or cationic polyelectrolyte molecules, existing either as one layer within multiple layers, or as a single layer of only one type of polyelectrolyte molecules on a wound or support. While the delivery of the polymers to the wound bed or support is sequential in preferred embodiments, the use of the term "polymer multilayer" is not limiting in terms of the resulting structure of the coating. It is well understood by those skilled in the art that inter-diffusion of polymers such as polyelectrolytes can take place leading to structures that may be well-mixed in terms of the distribution of anionic and cationic polyelectrolytes. It is also understood that the term polyelectrolyte includes polymer species as well as nanoparticulate species, and that it is not limiting in scope other than to indicate that the species possesses multiple charged or partially charged groups. It is also well understood by those skilled in the art that multilayer structures can be formed through a variety of interactions, including electrostatic interactions and others such as hydrogen bonding. Thus, the use of the term "polyelectrolyte" is not limiting in terms of the interactions leading to the formation of the wound bed constructs.

The term "subject" refers to any animal (e.g., a mammal), including, but not limited to, humans, non-human primates, rodents, dogs, cats, and the like, which is to be the recipient of a particular treatment. Typically, the terms "subject" and "patient" are used interchangeably herein.

The term "surfactant" refers to an amphiphilic material that modifies the surface and interface properties of liquids or solids. Surfactants can reduce the surface tension between two liquids. Detergents, wetting agents, emulsifying agents, dispersion agents, and foam inhibitors are all surfactants.

The term "solvent" refers to a liquid that can dissolve a substance. The term "organic solvent" refers to a solvent derived from a petroleum-based product.

The term "polyelectrolyte" refers to a water-soluble macromolecular polymer substance containing many repeating ionic constituent units, including cations and anions.

The term "functionalized" refers to a modification of an existing molecular segment to generate or introduce a new reactive functional group (e.g., a maleimido or succinimidyl group) that is capable of undergoing reaction with another functional group (e.g., a sulfhydryl group) to form a covalent bond. For example, a component containing carboxylic acid (—COOH) groups can be functionalized by reaction with N-hydroxy-succinimide or N-hydroxysulfosuccinimide using known procedures, to form a new reactive functional group in the form of an activated carboxylate (which is a reactive electrophilic group), i.e., an N-hydroxysuccinimide ester or an N-hydroxysulfosuccinimide ester, respectively. In another example, carboxylic acid groups can be functionalized by reaction with an acyl halide, e.g., an acyl chloride, again using known procedures, to provide a new reactive functional group in the form of an anhydride.

As used herein, the term "aqueous solution" includes solutions, suspensions, dispersions, colloids, and the like containing water.

The term "specific protein binding" refers to an interaction between two or more proteins that have high affinity and specificity for each other. Proteins must bind to specific other proteins in vivo in order to function. The proteins are required to bind to only one or a few other proteins of the few thousand proteins typically present in vivo; these interactions are employed in vitro in the present invention to attach bioactive agents to the wound. In the context of the present invention, specific protein binding interactions include, but are not limited to, those between biotin and avidin, neutravidin, or streptavidin; glutathione-S-transferase and glutathione; and nickel-nitrilotriacetic acid and polyhistidine.

The term "device" refers to an object that contacts the body or bodily fluid of a subject for therapeutic or prophylactic purposes. Some devices may partially or indirectly contact the body or bodily fluid of a subject (e.g., catheter, dialysis tubing, diagnostic sensors, drug delivery devices), while other devices are completely imbedded in or encompassed by the body of a subject (e.g., stent, pacemaker, internally implanted defibrillator, angioplasty balloon, orthopedic device, spinal cage, implantable drug pump, artificial disc, ear disc).

The term "selective toxicity" refers to the property of differentially toxic effects on mammalian versus microbial cells. For example, a selectively toxic agent may effectively kill bacterial cells while permitting growth and viability of mammalian cells.

The term "toxic" refers to any detrimental or harmful effects on a subject, a cell, or a tissue as compared to the same cell or tissue prior to the administration of the toxicant.

As used herein, the terms "nanoparticle" and "nanoscale particles" are used interchangeably and refer to a nanoscale particle with a size that is measured in nanometers, for example, a nanoscopic particle that has at least one dimension of less than about 1000, 500, or 100 nm. Examples of nanoparticles include nanobeads, nanofibers, nanohorns, nano-onions, nanorods, and nanoropes.

As used herein, the term "microparticle" and "microscale particles" are used interchangeably and refers to a microscale particle with a size that is measured in micrometers, for example, a microscale particle that has at least one dimension of less than about 10 micrometers, 5 micrometers, or 2 micrometers.

The term "wound dressing" refers to materials placed proximal to a wound that have absorbent, adhesive, protective, osmoregulatory, pH-regulatory, or pressure-inducing properties. Wound dressings may be in direct or indirect contact with a wound. Wound dressings are not limited by size or shape. Indeed, many wound dressing materials may be cut or configured to conform to the dimensions of a wound. Examples of wound dressing materials include but are not limited to gauze, adhesive tape, bandages, and commercially available wound dressings including but not limited to adhesive bandages and pads from the Band-Aid® line of wound dressings, adhesive bandages and pads from the Nexcare® line of wound dressings, adhesive bandages and non-adhesive pads from the Kendall Curity Tefla® line of wound dressings, adhesive bandages and pads from the Tegaderm® line of wound dressings, adhesive bandages and pads from the SteriStrip® line of wound dressings, the COMFEEL® line of wound dressings, adhesive bandages and pads, the Duoderm® line of wound dressings, adhesive bandages and pads, the TEGADERM™ line of wound dressings, adhesive bandages and pads, the OPSITE® line of wound dressings, adhesive bandages and pads, and biologic wound dressings. A "biologic wound dressing" is a type of wound dressing that comprises, e.g., is coated with or incorporates, cells and/or one or more biomolecules or fragments of biomolecules that can be placed in contact with the wound surface. The biomolecules may be provided in the form of an artificial tissue matrix. Examples of such biomolecules include, but are not limited, to collagen, hyaluronic acid, glycosaminoglycans, laminin, vitronectin, fibronectin, keratin, antimicrobial polypeptides and combinations thereof. Examples of suitable biologic wound dressings include, but are not limited to, BIOBRANE™, Integra™, Apligraf®, Dermagraft®, Oasis®, Transcyte®, Cryoskin® and Myskin®.

As used herein, the term "antimicrobial silver composition" refers to a composition that comprises silver as an active antimicrobial agent. Examples of "antimicrobial silver compositions" include, but are not limited to silver nanoparticles, elemental silver, zero valent silver, multivalent silver ions carried by zirconium phosphate (ZP—Ag) (See, e.g., Wound Repair and Regeneration, 16: 800-804), and silver containing compounds such as silver sulfadiazine and related compounds. The term "releasable antimicrobial silver composition" refers to an antimicrobial silver composition that can be released from a material, for example, a polymeric multilayer solid support, so that antimicrobial activity can be observed. The release of the antimicrobial silver composition can be defined as an amount of the composition released from a defined area or volume of the material.

DETAILED DESCRIPTION OF THE INVENTION

The present invention relates to large scale manufacture of nanoscale microsheets for use in applications such as wound healing or modification of a biological or medical surface. In some preferred embodiments, a substrate comprising a flexible polymeric sheet presenting a low surface energy surface is utilized in a continuous roll-to-roll layer-by-layer coating process for making a freestanding nano- or micro-scale polymeric film containing an active ingredient. The process is conducted at a large scale. Preferably the flexible polymeric sheet presenting a low surface energy surface provides a low surface energy surface having a surface area of at least 0.65, 1, 2, 5, 10, 100 or 500 square meters or from 0.65 to 1.0, 0.65 to 5.0, 0.65 to 10, 0.65 to 20, 0.65 to 50, 0.65 to 100, 0.65 to 200, 0.65 to 300, 0.65 to 400, 0.65 to 500, 1 to 10, 1 to 20, 1 to 50, 1 to 100, 1 to 200, 1 to 300, 1 to 400, 1 to 500, 2 to 10, 2 to 20, 2 to 50, 2 to 100, 2 to 200, 2 to 300, 2 to 400, 2 to 500, 5 to 10, 5 to 20, 5 to 50, 5 to 100, 5 to 200, 5 to 300, 5 to 400, 5 to 500, 10 to 20, 10 to 50, 10 to 100, 10 to 200, 10 to 300, 10 to 400, 10 to 500, 20 to 50, 20 to 100, 20 to 200, 20 to 300, 20 to 400, 20 to 500, 50 to 100, 50 to 200, 50 to 300, 50 to 400, or 50 to 500 square meters. Suitable techniques for coating the low surface energy surface of the substrate include, but are not limited to dip, immersion, spray, spin, slot die, inkjet, flexographic, gravure, reverse roll coating, metering (Meyer) rod, blade, air knife, curtain, melt extrusion, solvent casting and any combinations thereof. See, e.g., US PAT PUBL. 20140079884, US PAT PUBL. 20160068703, US PAT PUBL. 20120269973, US PAT PUBL. 20160114294, US PAT PUBL. 20140112994, US PAT PUBL. 20150086599, Shiratori, Japanese Journal of Applied Physics Vol. 44, No. 3, 2005, L126-L128, and Grunlan, Industrial & Engineering Chemistry Research Vol. 53, 2014, 6409-6416, all of which are incorporated herein by reference in their entirety. In general, the surfaces onto which polymer layers have been deposited at large scale have been high energy surfaces, for example, surfaces which been modified by plasma treatment. In the present invention, it has surprisingly been found that molecularly thin polymer layers may be deposited on large scale rolls of a substrate material in a continuous process so that defect-free molecularly thin polymeric sheets, preferably including a sacrificial layer, may be peeled from the substrate to provide a nano- to microscale polymeric sheet for use in application to a wound or for modification of a biological or medical surface. A bioactive agent is preferably incorporated into the nano- to microscale polymeric sheet to provide a desired level of release of a bioactive agent.

A. Substrates Having a Low Surface Energy Surface

In some embodiments, the present invention utilizes a substrate having a low surface energy surface as a substrate onto which a molecularly thin nano- or microscale polymer layer is deposited. In preferred embodiments, the substrate having a low surface energy surface is a flexible polymeric sheet. In some embodiments, the flexible polymeric sheet is amenable to storage and winding onto a roll for use in a continuous roll-to-roll process. As described above, the flexible polymeric sheet presenting a low surface energy surface provides a low surface energy surface having a surface area of at least 0.65, 1, 2, 5, 10, 100 or 500 square meters or from 0.65 to 1.0, 0.65 to 5.0, 0.65 to 10, 0.65 to 20, 0.65 to 50, 0.65 to 100, 0.65 to 200, 0.65 to 300, 00.65 to 400, 0.65 to 500, 1 to 10, 1 to 20, 1 to 50, 1 to 100, 1 to 200, 1 to 300, 1 to 400, 1 to 500, 2 to 10, 2 to 20, 2 to 50, 2 to 100, 2 to 200, 2 to 300, 2 to 400, 2 to 500, 5 to 10, 5 to 20, 5 to 50, 5 to 100, 5 to 200, 5 to 300, 5 to 400, 5 to 500, 10 to 20, 10 to 50, 10 to 100, 10 to 200, 10 to 300, 10 to 400, 10 to 500, 20 to 50, 20 to 100, 20 to 200, 20 to 300, 20 to 400, 20 to 500, 50 to 100, 50 to 200, 50 to 300, 50 to 400, or 50 to 500 square meters. The present invention is not limited to the use of any particular flexible polymeric sheets. Preferred materials include, but are not limited to, a polyester film, a polyethylene terephthalate (PET) film, a biaxially oriented PET film, a polycarbonate, a polyethylene (including high density polyethylene, medium density polyethylene, low density polyethylene, linear low density polyethylene) film, a polyvinyl chloride film, a polyvinylidene chloride film, a polyvinylidene fluoride film, a nylon film, a polystyrene film, an acetate film, a polyurethane film, an ethylene vinyl acetate copolymer film, a cast polypropylene film, an uniaxially oriented polypropylene film and a biaxially oriented polypropylene films. The preferred thickness of the sheet is from 0.5-5 mil. In some preferred embodiments, the flexible polymeric sheet has a surface having a surface energy of from 10 to 100 $mJ/cm^2$, and most preferably from about 15 to about 45 $mJ/cm^2$. In some embodiments, the low surface energy surface is provided by inclusion of a release film on the flexible polymeric sheet. In some embodiments, the release coating is a silicone release film, a polydimethyl siloxane (PDMS) coating, a fluorocarbon coating, a polyacrylate coating, a polystyrene coating, a polystyreneacrylic coating, a chromium sterate complex coating, or a polyolefin coating. Suitable release films include, but are not limited to, those provided St. Gobain Performance Plastics, Worcester MA, such as Saint Gobain 4130, 4159 and 7819 release coatings. In preferred embodiments, the release characteristics of the flexible polymeric sheet support the defect-free layer-by-layer deposition of polyelectrolytes as well as allowing facile and complete peeling of the wound dressing coating without tears or other defects thus resulting in a free standing polymeric film which can incorporate therapeutic agents such as antimicrobial agents and pain relievers as described in more detail below.

While some preferred embodiments have been described herein as utilizing flexible polymeric sheets, it will be understood that in some embodiments other materials may be substituted for the flexible polymeric sheet. Accordingly, in some embodiments, the substrate having a low surface energy surface may be preferably be a paper or cellulosic substrate such as glassine or supercalendered kraft paper coated with a release coating.

B. Nanoscale Polymer Layer

In preferred embodiments, the present invention provides a flexible polymeric sheet having a low surface energy surface as described above onto which a molecular thin, nano- to microscale polymer layer is deposited. In some embodiments, the nanoscale polymer layers, such as polymer multilayers, are nanoscale to microscale in dimension. Accordingly, in some embodiments, the nanoscale polymer matrices are from about 1 nm to 10000 nm thick, from about 1 nm to 5000 nm thick, from about 1 nm to 500 nm thick, from about 1 nm to 100 nm thick, from about 1 nm to about 25 nm thick, from about 1 nm to about 10 nm thick, or less than about 500 nm, 100 nm, 25 nm or 10 nm thick. It is contemplated that the nanoscale dimension of the matrices (i.e., the nanoscale thickness) allows for the loading of a lower total amount of an active agent while still allowing delivery of an effective amount (i.e., an amount of active agent that accelerates wound healing as compared to controls) of the active agent as compared to matrix structures with greater thickness. It is contemplated that the lower total loading levels result in reduced toxicity in the wound environment, especially when antimicrobial compounds are incorporated into the polymer multilayer.

In some embodiments, the present invention provides compositions comprising a nanoscale polymer layer that can be applied to a wound, a biologic tissue, a cornea, a lens, a bone, a tendon, a surgical mesh, a wound dressing, a biomedical device, a device used for healthcare, or other surface. In some embodiments, the nanoscale polymer layer is functionalized. In some embodiments, the nanoscale polymer layer is not functionalized. In some embodiments, the nanoscale polymer layer comprises one or more polymers, preferably biocompatible, or is formed from one or more proteins, or is a combination of polymers and proteins. In some embodiments, the nanoscale polymer layer is formed from synthetic polymers such as synthetic polyelectrolytes. In other embodiments, the nanoscale polymer layer is formed from naturally occurring polymers such as polysaccharides. In some embodiments, the nanoscale polymer layer is functionalized to allow for covalent interaction and/or binding to the tissue surface or the wound bed, or to allow application of bioactive agents to the nanoscale polymer layer. In some embodiments, a bioactive agent, for example an antimicrobial agent such as silver, polyhexamethylene biguanide (PHMB), chlorhexidine, or iodine compound, or an antibiotic, is incorporated into the nanoscale polymer layer. The bioactive agent is preferably impregnated, incorporated or interspersed throughout the three dimensional structure of the nanoscale polymer layer. For example, if the nanoscale polymer layer is polyelectrolyte multilayer (PEM), the bioactive agent is preferably incorporated between or within the layers of the polymer multilayer.

In some embodiments, the layer is a polymer multilayer. In some embodiments, the multilayer structures comprise layers of polyelectrolytes (i.e., forming a polyelectrolyte multilayer), while in other embodiments, the multilayers comprise polymers that do not have a charge (i.e., non-ionic polymers) or a combination of charged and uncharged polymer layers. In some embodiments, it is contemplated that polyelectrolyte films built-up by the alternated adsorption of cationic and anionic polyelectrolyte layers constitute a novel and promising technique to modify wound surfaces in a controlled way (Decher et al., 1992, Thin Solid Films 210/211:831; Decher, 1997, Science 277:1232). One of the most important properties of such multilayers is that they exhibit an excess of alternatively positive and negative charges (Caruso et al., 1999, J Am Chem Soc 121:6039; Ladam et al., 2000, Langmuir 16:1249). Not only can this constitute the motor of their buildup (Joanny, 1999, Eur. Phys. J. Biol. 9:117), but it allows, by simple contact, to adsorb a great variety of compounds such as dyes, particles (Cassagneau et al., 1998, J. Am. Chem. Soc. 120:7848; Caruso et al., 1999, Langmuir 15:8276; Lvov et al., 1997, Langmuir 13:6195), clay microplates (Ariga et al., 1999, Appl. Clay Sci. 15:137) and proteins (Keller et al., 1994, J. Am. Chem. Soc. 116:8817; Lvov et al., 1995, J. Am. Chem. Soc. 117:6117; Caruso et al., 1997, Langmuir 13:3427).

Polyelectrolyte layers are formed by alternating applications of anionic polyelectrolytes and cationic polyelectrolytes to surfaces to form a polyelectrolyte multilayer. In some embodiments, one or more bioactive agents, such as those described above, are incorporated into the multilayer. Preferably, at least four layers, and, more preferably, at least six layers are used to form the polyelectrolyte multilayer.

Cationic polyelectrolytes useful in the present invention can be any biocompatible water-soluble polycationic polymer, for example, any polymer having protonated heterocycles attached as pendant groups. As used herein, "water soluble" means that the entire polymer must be soluble in aqueous solutions, such as buffered saline or buffered saline with small amounts of added organic solvents as co-solvents, at a temperature between 20 and 37° Centigrade. In some embodiments, the material will not be sufficiently soluble (defined herein as soluble to the extent of at least one gram per liter) in aqueous solutions per se but can be brought into solution by grafting the polycationic polymer with water-soluble polynonionic materials such as polyethylene glycol.

Representative cationic polyelectrolytes include natural and unnatural polyamino acids having net positive charge at neutral pH, positively charged polysaccharides, and positively charged synthetic polymers. Examples of suitable polycationic materials include polyamines having amine groups on either the polymer backbone or the polymer side chains, such as poly-L-lysine (PLL) and other positively charged polyamino acids of natural or synthetic amino acids or mixtures of amino acids, including, but not limited to, poly(D-lysine), poly(ornithine), poly(arginine), and poly(histidine), and nonpeptide polyamines such as poly(aminostyrene), poly(aminoacrylate), poly (N-methyl aminoacrylate), poly (N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), and natural or synthetic polysaccharides such as chitosan.

In general, the polymers must include at least five charges, and the molecular weight of the polycationic material must be sufficient to yield the desired degree of binding to a tissue or other surface, having a molecular weight of at least 1000 g/mole.

Polyanionic materials useful in the present invention can be any biocompatible water-soluble polyanionic polymer, for example, any polymer having carboxylic acid groups attached as pendant groups. Suitable materials include alginate, carrageenan, furcellaran, pectin, xanthan, hyaluronic acid, heparin, heparan sulfate, chondroitin sulfate, polyacrylic acid (PAA), dermatan sulfate, dextran sulfate, poly(meth)acrylic acid, oxidized cellulose, carboxymethyl cellulose and crosmarmelose, synthetic polymers and copolymers containing pendant carboxyl groups, such as those containing maleic acid or fumaric acid in the backbone. Polyaminoacids of predominantly negative charge are also suitable. Examples of these materials include polyaspartic acid, polyglutamic acid, and copolymers thereof with other natural and unnatural amino acids. Polyphenolic materials such as tannins and lignins can be used if they are sufficiently biocompatible. Preferred materials include alginate, pectin, carboxymethyl cellulose, heparin and hyaluronic acid.

In some embodiments, the cationic polyelectrolyte used is PLL and the anionic polyelectrolyte used is poly(L-glutamic acid) (PGA). In some further preferred embodiments, the cationic polyelectrolyte used is polyallylamine hydrochloride (PAH) and the anionic polyelectrolyte used is poly-acrylic acid (PAA). Indeed, the use of a variety of polyelectrolytes is contemplated, including, but not limited to, poly (ethylene imine) (PEI), poly(sodium 4-styrenesulfonate) (PSS), poly(acrylic acid) (PAC), poly(maleic acid-co-propylene) (PMA-P), and poly(vinyl sulfate) (PVS). It is also possible to use naturally occurring polyelectrolytes, including hyaluronic acid and chondroitin sulfate. In still further embodiments, the polymer is a dendrimer, grafted polymer, or star architecture polymer.

In some embodiments, the multilayer structures are formed from uncharged polymers or from a combination of charged and uncharged polymers. Examples of uncharged polymers include, but are not limited to, dextran, dextran sulfate, diethylaminoethyl (DEAE)-dextran, hydroxyethyl cellulose, ethyl(hydroxyethyl) cellulose, acrylamide, polyethylene oxide, polypropylene oxide, polyethylene oxide-polypropylene oxide copolymers, $PAAN_a$, Ficoll, polyvinylpyrolidine, and polyacrylic acid.

In some embodiments, the multilayer structures are formed from one or more amphoteric polymers, alone in combination with the other polymers described herein. In some embodiments, the amphoteric polymers comprise one or more of acrylic acid (AA), DMAEMA (dimethylaminoethyl methacrylate), APA (2-aminopropyl acrylate), MorphEMA (morpholinoethyl methacrylate), DEAEMA (diethylaminoethyl methacrylate), t-ButylAEMA (t-butylaminoethyl methacrylate), PipEMA (piperidinoethyl methacrylate), AEMA (aminoethyl methacrylate), HEMA (2-hydroxyethyl methacrylate), MA (methyl acrylate), MAA (methacrylic acid) APMA (2-aminopropyl methacrylate), AEA (aminoethyl acrylate). In some embodiments, the amphoteric polymer comprises (a) carboxylic acid, (b) primary amine, and (c) secondary and/or tertiary amine. The amphoteric polymers have an isoelectric point of 4 to 8, preferably 5 to 7 and have a number average molecular weight in the range of 10,000 to 150,000.

Polymer layers may be formed on the low surface energy surface of the substrate by a variety of methods, including but not limited to the following techniques: spray coating, dip coating, immersion coating, spin coating, slot die coating, inkjet coating, anilox coating, screen coating, offset lithography printing, flexographic coating, gravure coating, rotogravure coating, reverse roll coating, metering (Meyer) rod coating, blade coating, knife over roll coating, air knife coating, curtain coating, melt extrusion coating, solvent casting and any combinations thereof. In some preferred embodiments, the flexible polymeric sheet is provided on a roll or is wound onto a roll. The leading edge of the sheet is then routed past one or more rolls (i.e., a series of rolls) and wound onto a receiving rolls. During this routing procedure, a primary layer-by-layer coating is deposited on low surface energy surface of the flexible polymeric sheet substrate by sequential deposition of at least two different materials of opposite charge from their solutions in suitable solvents. These polymers can be multivalent polymer salts and their solutions may contain univalent or multivalent organic or inorganic salts such as but not limited to chloride, sulfate, nitrate or acetate salts of univalent or divalent or trivalent metal cations in the concentration of 0.1-10000 mM and more preferably 0.5-50 mM. In some embodiments, the sheet is routed past one or more sprayers (i.e., a series of sprayers) and/or rinse basins and dryers. In other embodiments, the sheet is routed through one or more basins containing a polymer solution and/or one or more rinse basins and dryers. In some preferred embodiments, each polymer forming the polymer multilayer is deposited by allowing the flexible sheet substrate a residence time <600 seconds, preferably from 1-90 seconds, in the preferred solvent (e.g., an aqueous solution) followed by optional rinsing and drying. In some preferred embodiments, the thickness of final polymer multilayer coating is from 5-10000 nm, preferably from 5-5000 nm thick, and most preferably from 100-1000 nm thick. In some preferred embodiments, a bioactive agent, as described in more detail below, is then loaded into the polymer multilayer.

C. Second Polymer Layer

In some embodiments, a second polymer layer is deposited on or associated with the nano- to microscale polymer layer. In some preferred embodiments, the secondary polymer film has a thickness of from 1-50 µm, preferably 5-25 µm, and is coated onto the nano- to microscale polymer layer as described above for the deposition of the nano- to microscale polymer layer.

In some embodiments the nanoscale polymer matrix is supported by a second polymer layer, e.g., a non-sacrificial polymer layer. For example, in some embodiments, the nanoscale polymer matrix is supported by a second polymer layer, e.g., a non-sacrificial polymer layer, that comprises a hydrogel, a hydrocolloid, and/or collagen as a support.

In other embodiments, the nanoscale polymer matrix is supported on a sacrificial polymer layer, preferably a sacrificial polymer layer, formed from a degradable or dissolvable support material such as a dissolvable polymer. In preferred embodiments, sacrificial polymer layer of a microsheet is water soluble. In some embodiments, the sacrificial polymer layer is made of non-toxic polymer, and in some embodiments the sacrificial polymer layer is poly vinyl alcohol (PVA). In some embodiments the sacrificial polymer layer is made of polyacrylic acid (PAA), polyvinylpyrrolidone (PVP), carboxymethyl cellulose (CMC), sodium carboxymethyl cellulose, methylcellulose, ethylcellulose, ethylmethyl cellulose, hydroxyethyl cellulose (HEC), hydroxylpropyl cellulose (HPC), hydroxypropyl methylcellulose (HPMC), alginates, polyvinylacetate (PVAc), polylactic acid (PLA), polylactic-co-glycolic acid (PLGA), polyglycolic acid, or polyanhydrides. In some embodiments, the nanoscale polymer layer is first formed on a solid support as described above and then a sacrificial polymer layer is formed on the nanoscale polymer matrix, for example, by spray coating, spin coating, slot die coating, anilox coating, screen coating, inkjet coating, offset lithography printing, flexographic coating, gravure coating, rotogravure coating, reverse roll coating, metering (Meyer) rod coating, blade coating, knife over roll coating, air knife coating, curtain coating, melt extrusion coating, solvent casting and any combinations thereof. In preferred embodiments, the sacrificial polymer layer material is dissolvable in aqueous environments or environments where moisture is present, such as moist surfaces like wound beds, internal body surfaces, epithelial surfaces and the like. In preferred embodiments, the sacrificial polymer layer material is dissolvable in aqueous solutions after application of the nanoscale polymer matrix on the surface. In some embodiments, the sacrificial polymer layer is microscale in dimension, and may range from 0.2 µm to 1000 µm, 0.2 µm to 500 µm, 0.2 µm to 200 µm, 0.2 µm to 100 µm, 1 µm to 50 µm, 1 µm to 20 µm, 0.2 µm to 10 µm or 1 µm to 10 µm, and is preferably less than 100, 50, 20, or 10 µm in thickness.

In some embodiments, a freestanding film is obtained by peeling the combined nano- to microscale polymer layer and second polymer layer from the substrate. This freestanding film comprising a nano- to microscale polymer layer adjacent to a second polymer layer may be referred to as a microsheet. In some embodiments, the substrate supporting the combined nano- to microscale polymer layer and second polymer layer is cut to a predetermined size and/or state before the microsheet is peeled away. In some embodiments, sacrificial polymer layer of a microsheet contains bioactive agents, antimicrobial agents, antibiofilm agents, microparticles, nanoparticles, magnetic particles as described in more detail below. In some embodiments, microparticles or nanoparticles in the sacrificial polymer layer contain bioactive agents or antimicrobial agents. In some embodiments, the second polymer layer comprises an antibiofilm agent. The technology is not limited in the antibiofilm agent that is used in embodiments of the device and associated method, kit, and method of treatment embodiments. For example, in some embodiments the antibiofilm agent is a small molecule antibiofilm agent, a charged small molecule antibiofilm agent, an antibiofilm polypeptide, an antibiofilm enzyme (e.g., Dispersin B), a metallic particle, or a metal ion antibiofilm agent (e.g., a metal ion, metal ion salt, or metal ion nanoparticle). Further, in some embodiments, the metal ion antibiofilm agent is a gallium ion, a gallium ion salt, a gallium ion nanoparticle, an alloy of gallium, or an alloy of gallium and silver.

D. Bioactive Agents

In some embodiments, the nano- to microscale polymeric sheets may function as a drug delivery scaffold to deliver one or more bioactive agents to the wound. Bioactive agents that may be desirable to deliver include, but are not limited to, trophic factors, extracellular matrices (ECMs), ECM fragments or synthetic constructs, enzymes, enzyme inhibitors, defensins, polypeptides, anti-infective agents (including antimicrobials, antivirals and antifungals), buffering agents, vitamins and minerals, analgesics, anticoagulants, coagulation factors, anti-inflammatory agents, vasoconstrictors, vasodilators, diuretics, and anti-cancer agents. In addition, would active agents include chlorhexidine, iodine based antimicrobials such as PVP-iodine; selenium based antimicrobials such as 7-azabenzisoselenazol-3(2H)-ones, selenium disulfide, and selenides; silver based antimicrobials (e.g., silver sulfadiazine, ionic silver, elemental silver, silver nanoparticles)) and gallium based antimicrobials. With respect to selenides, with the use of standard and variations of typical protein and carbohydrate attachment chemistries, carboxyl and amino containing selenides may be routinely attached to many polymers, peptides, antibodies, steroids and drugs. Polymers and other molecules with attached selenides generate superoxide in a dose dependent manner in biological solutions, in cells or attached to insoluble matrixes such as silicones.

A wide variety of bioactive agents can be incorporated into the polyelectrolyte layer or second polymer layer, referred to collectively as the microsheet. The present invention is not limited to a particular mechanism by which one or more bioactive agents are released from the microsheet. Indeed, an understanding of the mechanism is not necessary to practice the present invention. Nonetheless, in some embodiments, the present invention contemplates release of the one or more incorporated agents from the microsheet layers to the wound by diffusion from the polyelectrolyte layer. In other embodiments, the one or more bioactive agents may be released from the microsheet layers over time or in response to an environmental condition. The one or more bioactive agents may be attached by a degradable linkage, such as a linkage susceptible to degradation via hydrolysis or enzymatic degradation. The linkage may be one that is susceptible to degradation at a certain pH, for example.

In some embodiments, the one or more bioactive agents are applied to form a gradient with respect to the wound modifying agent. In general, the gradients present a higher contraction of bioactive agent at one or more first desired locations in the wound following application of the wound modifying agent to the wound and a lower concentration of bioactive agent at one or second location in the wound following application of the wound modifying agent to the wound. For example, the concentrations of the bioactive agents are layered in a wound bed in a gradient such that higher concentrations of a particular composition is greater proximal to the wound bed than distal to the wound bed in a vertical fashion. The converse, where concentrations of compositions is greater distal to the wound bed than proximal, is also contemplated. Concentration of compositions in a wound bed wherein a horizontal gradient is deposited is also contemplated. Topographical gradients are also contemplated, wherein compositions are deposited such that the concentrations of compositions in a wound bed or on a biocompatible particle follow the topography of the substrate, for example, a higher concentration of compositions is deposited in the valleys of undulations of an exemplary substrate compared to the peaks of the undulations.

In some embodiments, the gradient comprises a higher concentration of the bioactive agent in the center of the wound modifying agent which transitions to a lower concentration of the bioactive agent away from the center of the wound modifying agent. Accordingly, when the wound modifying agent is applied to a wound, the gradient results in a higher concentration of bioactive agent in the center of the wound and a lower concentration of bioactive agent as one moves to the periphery of the wound. In some embodiments, the gradient comprises a lower concentration of the bioactive agent in the center of the wound modifying agent which transitions to a higher concentration of the bioactive agent away from the center of the wound modifying agent. Accordingly, the gradient results in a lower concentration of bioactive agent in the center of the wound and a higher concentration of bioactive agent as one moves to the periphery of the wound. If two or more bioactive agents are utilized, they can be presented as similar gradients or the gradients can be varied so that the concentrations of the two or more bioactive agents vary across the wound. The gradients of high or low concentration can be any shape, such as circular, square, rectangular, oval, oblong, etc. so that the matrix and gradient can conform to a variety of wound shapes. For example, for long, incision type wound, the gradient may be centered on a longitudinal axis that extends along the length of the wound and can be centered on the wound. As another example, the gradient can be circular or oval-shaped for application to open type wounds, burns, sores and ulcers that are roughly circular or oval. In other embodiments, the gradients comprise a series of features arranged in a pattern. For example, the gradients can form a series of stripes or high and low concentrations of one or more bioactive agents along a longitudinal axis of the matrix. Alternatively, the gradients can form a checkerboard pattern, array, concentric circles, overlapping circles or oval, etc.

The present invention contemplates delivery of a wide variety of bioactive agents to the wound. In some embodiments, the present invention provides the delivery of trophic factors, including, but not limited to, agrin, amphiregulin, artemin, cardiotrophin-1, epidermal growth factors including EGF; fibroblast growth factors (e.g., FGF-1, FGF-2, FGF-3, FGF-4, FGF-5, FGF-6, and FGF-7); LIF, CSF-1, CSF-2, CSF-3, erythropoietin, endothelial cell growth factors including ECGF; FGF-related and ECGF-related growth factors (e.g., endothelial cell stimulating angiogenesis factor, tumor angiogenesis factor, retina-derived growth factor (RDGF), vascular endothelium growth factor (VEGF), brain-derived growth factors (BDGF-A and B), astroglial growth factors (AGF 1 and 2), omentum-derived growth factor, fibroblast-stimulating factor (FSF), and embryonal carcinoma-derived growth factor (ECDGF)); neurotrophic growth factors (e.g, nerve growth factors (NGFs), neurturin, brain-derived neurotrophic factor (BDNF), neurotrophin-3, neurotrophin-4, and ciliary neurotrophic factor (CNTF)); glial growth factors (e.g., GGF-I, GGF-II, GGF-III, glia maturation factor (GMF), and glial-derived neurotrophic factor (GDNF)); liver growth factors (e.g., hepatopoietin A, hepatopoietin B, and hepatocyte growth factors including HGF); prostate growth factors including prostate-derived growth factors (PGFs); mammary growth factors including mammary-derived growth factor 1 (MDGF-1) and mammary tumor-derived factor (MTGF); heart growth factors including nonmyocyte-derived growth factor (NMDGF); melanocyte growth factors including melanocyte-stimulating hormone (MSH) and melanoma growth-stimulating activity (MGSA); angiogenic factors (e.g., angiogenin, angiotropin, platelet-derived ECGF, VEGF, and pleiotrophin); transforming growth factors including TGF-α and TGF-β; TGF-like growth factors (e.g., TGF-beta$_1$, TGF-beta$_2$, TGF-beta$_3$, GDF-1, CDGF, tumor-derived TGF-like factors, ND-TGF, and human epithelial transforming factor); regulatory peptides with growth factor-like properties (e.g., bombesin and bombesin-like peptides ranatensin and litorin, angiotensin, endothelin, atrial natriuretic factor, vasoactive intestinal peptide, and bradykinin); platelet-derived growth factors including PDGF-A, PDGF-B, and PDGF-AB; neuropeptides (e.g., substance P, calcitonin gene-regulated peptide (CGRP), and neuropeptide Y); neurotransmitters and their analogs including norepinephrine, acetylcholine and carbachol; hedgehog, heregulin/neuregulin, IL-1, osteoclast-activating factor (OAF), lymphocyte-activating factor (LAF), hepatocyte-stimulating factor (HSF), B-cell-activating factor (BAF), tumor inhibitory factor 2 (TIF-2), keratinocyte-derived T-cell growth factor (KD-TCGF), IL-2, IL-3, IL-4, IL-5, IL-6, IL-7, IL-8, IL-9, IL-10, IL-11, stromal cell-derived cytokine (SCDC), IL-12, IL-13, IL-14, IL-15, insulin, insulin-like growth factors including IGF-1, IGF-2, and IGF-BP; interferons including INF-alpha, INF-beta, and INF-gamma; leptin, midkine, tumor necrosis factors (TNF-alpha and beta), netrins, saposins, semaphorins, somatrem, somatropin, stem cell factor, VVGF, bone morphogenetic proteins (BMPs), adhesion molecules, other cytokines, heparin-binding growth factors, and tyrosine kinase receptor ligands. In some embodiments, the bioactive agent is a peptide such as AcEEED, which is the N terminal peptide for alpha smooth muscle actin and has been shown to inhibit contractile properties of myofibroblasts.

In some embodiments, the present invention provides the delivery of ECMs, including, but not limited to native constructs, fragments of native constructs and synthetic analogs of: extracellular matrix proteins, reconstituted basement membrane-like complexes derived from eukaryotic cell lines, collagens, fibronectin, laminin, VCAM-1, vitronectin and gelatin, a bacterial extracellular matrix, a gel matrix, and polymeric matrices. In some embodiments, the bioactive agents are integrin binding sequences exemplified by, but not limited to RGD, EILDV, VCAM-1 and their recombined or synthetic analogs, enzymes, enzyme inhibitors, and polypeptides.

In some embodiments, the present invention provides the delivery of enzymes, including, but not limited to, exopeptidases and endopeptidases (also known as proteases and proteinases), including but not limited to the serine proteinases chymotrypsin, trypsin, elastase, and kallikrein, bacterial enzymes, the cysteine proteases papain, actinin, bromelain, cathepsins, cytosolic calpains, parasitic proteases, aspartic proteinases, the pepsin family of proteases pepsin and chymosin, lysosomal cathepsins D, renin, fungal proteases, the viral proteases, AIDS virus retropepsin, and the metalloproteinases (MMPs), collagenases, Maggott enzyme, MMP1, MMP2, MMP8, MMP13, gelatinases, MMP2, MMP9, MMP3, MMP7, MMP10, MMP11, and MMP12.

In some embodiments, the present invention provides the delivery of enzyme inhibitors, including, but not limited to captopril, thiorphan, phosphoramidon, teprotide, protease and proteinase inhibitors, metalloproteinase inhibitors and exopeptidase inhibitors.

In some embodiments, the present invention provides the delivery of defensins, including, but not limited to, alpha-defensins HNP 1, 2, 3 and 4, and beta-defensins HBD-1 and HBD-2.

In some embodiments, the present invention provides the delivery of polypeptides, including, but not limited to, fibronectin, serotonin, PAF, PDEGF, TNFa, IL1, IL6, IGF, IGF-1, IGF-2, IL-1, PDGF, FGF, KGF, VEGF, bradykinin, prothymosin-alpha, and thymosin-alpha1.

In some embodiments, the present invention provides the delivery of antimicrobials, including, but not limited to, magainin (e.g., magainin I, magainin II, xenopsin, xenopsin precursor fragment, caerulein precursor fragment), magainin I and II analogs (e.g., PGLa, magainin A, magainin G, pexiganin, Z-12, pexigainin acetate, D35, MSI-78A, MG0 (K10E, K11E, F12W-magainin 2), MG2+ (K10E, F12W-magainin-2), MG4+(F12W-magainin 2), MG6+ (f12W, E19Q-magainin 2 amide), MSI-238, reversed magainin II analogs (e.g., 53D, 87-ISM, and A87-ISM), Ala-magainin II amide, magainin II amide), cecropin P1, cecropin A, cecropin B, indolicidin, nisin, ranalexin, lactoferricin B, poly-L-lysine, cecropin A (1-8)-magainin II (1-12), cecropin A (1-8)-melittin (1-12), CA(1-13)-MA(1-13), CA(1-13)-ME (1-13), gramicidin, gramicidin A, gramicidin D, gramicidin S, alamethicin, protegrin, histatin, dermaseptin, lentivirus amphipathic peptide or analog, parasin I, lycotoxin I or II, globomycin, gramicidin S, surfactin, ralinomycin, valinomycin, polymyxin B, PM2 ((+/−) 1-(4-aminobutyl)-6-benzylindane), PM2c ((+/−) -6-benzyl-1-(3-carboxypropyl)indane), PM3 ((+/−) 1-benzyl-6-(4-aminobutyl)indane), tachyplesin, buforin I or II, misgurin, melittin, PR-39, PR-26, 9-phenylnonylamine, (KLAKKLA)n, (KLAKLAK)n, where n=1, 2, or 3, (KALKALK)3, KLGKKLG)n, and KAAKKAA)n, wherein N=1, 2, or 3, paradaxin, Bac 5, Bac 7, ceratoxin, mdelin 1 and 5, bombin-like peptides, PGQ, cathelicidin, HD-5, Oabac5alpha, ChBac5, SMAP-29, Bac7.5, lactoferrin, granulysin, thionin, hevein and knottin-like peptides, MPG1, 1bAMP, snakin, lipid transfer proteins, and plant defensins. Exemplary sequences for the above compounds are provided in Table 1. In some embodiments, the antimicrobial peptides are synthesized from L-amino acids, while in other embodiments, the peptides are synthesized from, or comprise, D-amino acids.

TABLE 1

Antimicrobial Peptides

| SEQ ID NO: | Name | Organism | Sequence |
|---|---|---|---|
| 1 | lingual antimicrobial peptide precursor (Magainin) | Bos taurus | mrlhhlllallflvlsagsgftqgvrnsqserrnkgicvpircpgsmrqigtclgaqvkccrrk |
| 2 | antimicrobial peptide PGQ | Xenopus laevis | gvlsnvigylkklgtgalnavlkq |
| 3 | Xenopsin | Xenopus laevis | mykgiflcvllavicanslatpssdadednderveryvrgwaskigqtlgkiakvglkeliqpkreamlrsaeaqgkrpwil |
| 4 | magainin precursor | Xenopus laevis | mfkglficsliavicanalpqpeasadedmderevrgigkflhsagkfgkafvgeimkskrdaeavgpeafadedlderevrgigkflhsakkfgkafvgeimnskrdaeavgpeafadedlderevrgigkflhsakkfgkafvgeimnskrdaeavgpeafadedlderevrgigkflhsakkfgkafvgeimnskrdaeavgpeafadedfderevrgigkflhsakkfgkafvgeimnskrdaeavgpeafadedlderevrgigkflhsakkfgkafvgeimnskrdaeavddrrwve |
| 5 | tachyplesin I | Tachypleus gigas | kwcfrvcyrgicyrrer |
| 6 | tachyplesin II | Tachypleus gigas | rwcfrvcyrgicyrker |
| 7 | buforin I | Bufo bufo gagarizans | msgrgkqggkvrakaktrssraglqfpvgrvhrllrkgnyaqrvgagapvylaavleyltaeilelagnaardnkktriiprhlqlavrndeelnkllggvtiaqggvlpniqavllpktesskpaksk |
| 8 | buforin II | Bufo bufo gagarizans | trssraglqfpvgrvhrllrk |
| 9 | cecropin A | Bombyx mori | mnfvrilsfvfalvlalgavsaapeprwklfkkiekvgrnvrdglikagapaiavigqakslgk |
| 10 | cecropin B | Bombyx mori | mnfakilsfvfalvlalsmtsaapeprwkifkkiekmgrnirdgivkagapaievlgsakaigk |
| 11 | cecropin C | Drosophila melanogaster | mnfykifvfvalilaisigqseagwlkklgkrierigqhtrdatiqglgiaqqaanvaatarg |
| 12 | cecropin P1 | Sus scrofa | swlsktakklensakkrisegiaiaiqggpr |
| 13 | indolicidin | Bos taurus | ilpwkwpwwpwrr |
| 14 | nisin | Lactococcus lactis | itsislctpgcktgalmgenmktatchcsihvsk |
| 15 | ranalexin | Rana catesbeiana | flgglikivpamicavtkkc |
| 16 | lactoferricin B | Bos taurus | fkcrrwqwrmkklgapsitcvrraf |
| 17 | protegrin-1 | Sus scrofa | rggrlcycrrrfcvcvgrx |
| 18 | protegrin-2 | Sus scrofa | ggrlcycrrrfcicvg |
| 19 | histatin precursor | Homo sapiens | mkffvfalilalmlsmtgadshakrhhgykrkfhekhhshrgyrsnylydn |
| 20 | histatin 1 | Macaca fascicularis | dsheerhhgrhghhkygrkfhekhhshrgyrsnylydn |
| 21 | dermaseptin | Phyllomedusa sauvagei | alwktmlkklgtmalhagkaalgaaadtisqtq |
| 22 | dermaseptin 2 | Phyllomedusa sauvagei | alwftmlkklgtmalhagkaalgaaantisqgtq |
| 23 | dermaseptin 3 | Phyllomedusa sauvagei | alwknmlkgigklagkaalgavkklvgaes |
| 24 | misgurin | Misgurnus anguillicaudatus | rqrveelskfskkgaaarrk |

TABLE 1-continued

Antimicrobial Peptides

| SEQ ID NO: | Name | Organism | Sequence |
|---|---|---|---|
| 25 | melittin | *Apis mellifera* | gigavlkvlttglpaliswisrkkrqq |
| 26 | pardaxin-1 | *Pardachirus pavoninus* | gffalipkiissplfktllsavgsalsssgeqe |
| 27 | pardaxin-2 | *Pardachirus pavoninus* | gffalipkiisspifktllsavgsalsssggqe |
| 28 | bactenecin 5 precursor | *Bos taurus* | metqraslslgrcslwllllglvlpsasaqalsyreavlr avdqfnersseanlyrllleldptpnddldpgtrkpvsfrv ketdcprtsqqpleqcdfkenglvkqcvgtvtldpsndqf dincnelqsvrfrppirrppirppfyppfrppirppifpp irppfrpplgpfpgrr |
| 29 | bactenecin precursor | *Bos taurus* | metpraslslgrwslwllllglalpsasaqalsyreavlr avdqlneqssepniyrlleldqppqddedpdspkrvsfrv ketvcsrttqqppeqcdfkengllkrcegtvtldqvrgnf ditcnnhqsiritkqpwappqaarlcrivvirver |
| 30 | ceratotoxin A | *Ceratitis capitata* | sigsalkkalpvakkigkialpiakaalp |
| 31 | ceratotoxin B | *Ceratitis capitata* | sigsafkkalpvakkigkaalpiakaalp |
| 32 | cathelicidin antimicrobial peptide | *Homo sapiens* | mktqrnghslgrwslvllllglvmplaiiaqvlsykeavl raidginqrssdanlyrlldldprptmgdgpdtpkpvsft vketvcprttqqspedcdfkkdglvkrcmgtvtlnqargs fdiscdkdnkrfallgdffrkskekigkefkrivqrikdf lrnlvprtes |
| 33 | myeloid cathelicidin 3 | *Equus caballus* | metqrntrclgrwspllllglvippattqalsykeavlr avdglnqrssdenlyrlleldplpkgdkdsdtpkpvsfmv ketvcprimkqtpeqcdfkenglvkqcvgtvildpvkdyf dascdepqrvkrfhsvgsliqrhqqmirdkseatrhgiri itrpklllas |
| 34 | myeloid antimicrobial peptide BMAP-28 | *Bos taurus* | metqraslslgrwslwllllglalpsasaqalsyreavlr avdqlnekssseanlyrlleldpppkeddenpnipkpvsfr vketvcprtsqqspeqcdfkengllkecvgtvtldqvgsn fditcavpqsvgglrslgrkilrawkkygpiivpiirig |
| 35 | myeloid cathelicidin 1 | *Equus caballus* | metqrntrclgrwspllllglvippattqalsykeavlr avdglnqrssdenlyrlleldplpkgdkdsdtpkpvsfmv ketvcprimkqtpeqcdfkenglvkqcvgtvilgpvkdhf dvscgepqrvkrfgrlaksflrmrillprrkillas |
| 36 | SMAP 29 | *Ovis aries* | metqraslslgrcslwllllglalpsasaqvlsyreavlr aadqlneksseanlyrlleldpppkqddensnipkpvsfr vketvcprtsqqpaeqcdfkengllkecvgtvtldqvrnn fditcaepqsvrglrrlgrkiahgvkkygptvlriiriag |
| 37 | BNP-1 | *Bos taurus* | rlcrivvirvcr |
| 38 | HNP-1 | *Homo sapiens* | acycripaciagerrygtciyqgrlwafcc |
| 39 | HNP-2 | *Homo sapiens* | cycripaciagerry gtciyqgrlwafcc |
| 40 | HNP-3 | *Homo sapiens* | dcycripaciagerrygtciyqgrlwafcc |
| 41 | HNP-4 | *Homo sapiens* | vcscrlvfcrrtelrvgncliggvsftycctrv |
| 42 | NP-1 | *Oryctolagus cuniculus* | vvcacrralclprerragfcrirgrihplccrr |
| 43 | NP-2 | *Oryctolagus cuniculus* | vvcacrralclplerragfcrirgrihplccrr |
| 44 | NP-3A | *Oryctolagus cuniculus* | gicacrrrfcpnserfsgycrvngaryvrccsrr |
| 45 | NP-3B | *Oryctolagus cuniculus* | grevcrkqllcsyrerrigdckirgvrfpfccpr |

TABLE 1-continued

Antimicrobial Peptides

| SEQ ID NO: | Name | Organism | Sequence |
|---|---|---|---|
| 46 | NP-4 | Oryctolagus cuniculus | vsctcrrfscgfgerasgsctvnggvrhtlccrr |
| 47 | NP-5 | Oryctolagus cuniculus | vfctcrgflcgsgerasgsctingvrhtlccrr |
| 48 | RatNP-1 | Rattus norvegicus | vtcyerrtregfrerlsgacgyrgriyrlccr |
| 49 | Rat-NP-3 | Rattus norvegicus | cscrysscrfgerllsgacrlngriyrlcc |
| 50 | Rat-NP-4 | Rattus norvegicus | actcrigacvsgerltgacglngriyrlccr |
| 51 | GPNP | Guinea pig | rrcicttrtcrfpyrrlgtcifqnrvytfcc |
| 52 | beta defensin-3 | Homo sapiens | mrihyllfallflflvpvpghggiintlqkyycrvrggrc avlsclpkeeqigkcstrgrkccrrkk |
| 53 | theta defensin-1 | Macaca mulatta | rcictrgfcrclerrgvc |
| 54 | defensin CUA1 | Helianthus annuus | mkssmkmfaallllvvmcllanemggplvveartcesqshk fkgtclsdtncanvchserfsggkcrgfrrrcfctthc |
| 55 | defensin SD2 | Helianthus annuus | mkssmkmfaallllvvmcllanemggplvveartcesqshk fkgtclsdtncanvchserfsggkcrgfrrrcfctthc |
| 56 | neutrophil defensin 2 | Macaca mulatta | acycripaclagerrygtcfymgrvwafcc |
| 57 | 4 KDA defensin | Androctonus australis hector | gfgcpfnqgachrhcrsirrrggycaglfkqtctctcyr |
| 58 | defensin | Mytilus galloprovincialis | gfgcpnnyqchrhcksipgroggycggxhrlrctcyrc |
| 59 | defensin AMP1 | Heuchera sanguinea | dgvklcdvpsgtwsghcgssskcsqqckdrehfayggach yqfpsvkcfckrqc |
| 60 | defensin AMP1 | Clitoria ternatea | nlcerasltwtgncgntghcdtqcrnwesakhgachkrgn wkcfcyfnc |
| 61 | cysteine-rich cryptdin-1 homolog | Mus musculus | mkklvllfalvllafqvqadsiqntdeetkteeqpgekdq avsvsfgdpqgsalqdaalgwgrrcpqcprepscpscprc prcprckcnpk |
| 62 | beta-defensin-9 | Bos taurus | qgvrnfvtcrinrgfcvpircpghrrqigtclgpqikccr |
| 63 | beta-defensin-7 | Bos taurus | qgvrnfvtcrinrgfcvpircpghrrqigtelgprikccr |
| 64 | beta-defensin-6 | Bos taurus | qgvrnhvtcriyggfcvpircpgrtrqigtcfgrpvkccrrw |
| 65 | beta-defensin-5 | Bos taurus | qvvrnpqscrwnmgvcipiscpgnmrqigtcfgprvpccr |
| 66 | beta-defensin-4 | Bos taurus | qrvrnpqscrwnmgvcipflervgmrqigtcfgprvpccrr |
| 67 | beta-defensin-3 | Bos taurus | qgvrnhvtcrinrgfcvpircpgrtrqigtcfgprikccrsw |
| 68 | beta-defensin-10 | Bos taurus | qgvrsylscwgnrgiclnrcpgrmrqigtclaprvkccr |
| 69 | beta-defensin-13 | Bos taurus | sgisgplscgrnggvcipircpvpmrqigtcfgrpvkccrsw |
| 70 | beta-defensin-1 | Bos taurus | dfaschtnggiclpnrcpghmiqigicfrprvkccrsw |
| 71 | coleoptericin | Zophobas atratus | slqggapnfpqpsqqnggwqvspdlgrddkgntrgqieiq nkgkdhdfnagwgkvirgpnkakptwhvggtyrr |
| 72 | beta defensin-3 | Homo sapiens | mrihyllfallflflvpvpghggiintlqkyycrvrggrc avlsclpkeeqigkcstrgrkccrrkk |
| 73 | defensin C | Aedes aegypti | atcdllsgfgvgdsacaahciargnrggycnskkvcvcrn |
| 74 | defensin B | Mytilus edulis | gfgcpndypchrhcksipgryggycggxhrlrctc |

TABLE 1-continued

Antimicrobial Peptides

| SEQ ID NO: | Name | Organism | Sequence |
|---|---|---|---|
| 75 | sapecin C | Sarcophaga peregrina | atcdllsgigvqhsacalhcvfrgnrggyctgkgicvcrn |
| 76 | macrophage antibiotic peptide MCP-1 | Oryctolagus cuniculus | mrtlallaaillvalqaqaehvsvsidevvdqqppqaedq dvaiyvkehessalealgvkagvvcacrralclprerrag fcrirgrihplccrr |
| 77 | cryptdin-2 | Mus musculus | mkplvllsalvllsfqvqadpiqntdeetkteeqsgeedq avsvsfgdregaslqeeslrdlvcycrtrgckrrermngt crkghlmytlcc |
| 78 | cryptdin-5 | Mus musculus | mktfvllsalvllafqvqadpihktdeetnteeqpgeedq avsisfggqegsalheelskklicycrirgckrrervfgt crnlfltfvfccs |
| 79 | cryptdin 12 | Mus musculus | lrdlvcycrargckgrermngtcrkghllymlccr |
| 80 | defensin | Pyrrhocoris apterus | atcdilsfqsqwvtpnhagcalhcvikgykggckitvchcrr |
| 81 | defensin R-5 | Rattus norvegicus | vtcycrstregfrerlsgacgyrgriyrlccr |
| 82 | defensin R-2 | Rattus norvegicus | vtcscrtsscrfgerlsgacrlngriyrlcc |
| 83 | defensin NP-6 | Oryctolagus cuniculus | gicacrrrfclnfeqfsgycrvngaryvrccsrr |
| 84 | beta-defensin-2 | Pan troglodytes | mrvlyllfsflfiflmplpgvfggisdpvtclksgaichp vfcprrykqigtcglpgtkcckkp |
| 85 | beta-defensin-2 | Homo sapiens | mrvlyllfsflfiflmplpgvfggigdpvtclksgaichp vfcprrykqigtcglpgtkcckkp |
| 86 | beta-defensin-1 | Homo sapiens | mrtsylllftlclllsemasggnfltglghrsdhyncvss ggqclysacpiftkiqgtcyrgkakcck |
| 87 | beta-defensin-1 | Capra hircus | mrlhhlllvlfflvlsagsgftqgirsrrschrnkgvcal trcprnmrqigtcfgppvkccrkk |
| 88 | beta defensin-2 | Capra hircus | mrlhhlllalfflvlsagsgftqgiinhrscyrnkgvcap arcprnmrqigtchgppvkccrkk |
| 89 | defensin-3 | Macaca mulatta | mrtlvilaaillvalqaqaeplqartdeataaqeqiptdn pevvvslawdeslapkdsvpglrknmacycripaclager rygtcfyrrrvwafcc |
| 90 | defensin-1 | Macaca mulatta | mrtlvilaaillvalqaqaeplqartdeataaqeqiptdn pevvvslawdeslapkdsvpglrknmacycripaclager rygtcfylgrvwafcc |
| 91 | neutrophil defensin 1 | Mesocricetus auratus | vtcfcrrrgcasrerhigycrfgntiyrlccrr |
| 92 | neutrophil defensin 1 | Mesocricetus auratus | cfckrpvcdsgetqigycrlgntfyrlccrq |
| 93 | Gallinacin 1-alpha | Gallus gallus | grksdcfrkngfcaflkcpyltlisgkcsrfhlcckriw |
| 94 | defensin | Allomyrina dichotoma | vtcdllsfeakgfaanhslcaahclaigrrggscergvcicrr |
| 95 | neutrophil cationic peptide 1 | Cavia porcellus | rrcicttrtcrfpyrrlgtcifqnrvytfcc |

In some embodiments, the present invention provides the delivery of antimicrobials, including, but not limited to, loracarbef, cephalexin, cefadroxil, cefixime, ceftibuten, cefprozil, cefpodoxime, cephradine, cefuroxime, cefaclor, neomycin/polymyxin/bacitracin, dicloxacillin, nitrofurantoin, nitrofurantoin macrocrystal, nitrofurantoin/nitrofuran mac, dirithromycin, gemifloxacin, ampicillin, gatifloxacin, penicillin V potassium, ciprofloxacin, enoxacin, amoxicillin, amoxicillin/clavulanate potassium, clarithromycin, levofloxacin, moxifloxacin, azithromycin, sparfloxacin, cefdinir, ofloxacin, trovafloxacin, lomefloxacin, methenamine, erythromycin, norfloxacin, clindamycin/benzoyl peroxide, quinupristin/dalfopristin, doxycycline, amikacin sulfate, vancomycin, kanamycin, netilmicin, streptomycin, tobramycin sulfate, gentamicin sulfate, tetracyclines, framycetin, minocycline, nalidixic acid, demeclocycline, trimethoprim, miconazole, colistimethate, piperacillin sodium/tazobactam sodium, paromomycin, colistin/neomycin/hydrocortisone, amebicides, sulfisoxazole, pentamidine, sulfadiazine, clindamycin phosphate, metronidazole, oxacillin sodium, nafcillin sodium, vancomycin hydrochloride, clindamycin, cefotaxime sodium, co-trimoxazole, ticarcillin disodium, piperacillin sodium, ticarcillin disodium/clavulanate potassium, neomycin, daptomycin, cefazolin sodium, cefoxitin sodium, ceftizoxime sodium, penicillin G potassium and sodium, ceftriaxone sodium, ceftazidime, imipenem/cilastatin sodium, aztreonam, cinoxacin, erythromycin/sulfisoxazole, cefotetan disodium, ampicillin sodium/sulbactam sodium, cefoperazone sodium, cefamandole nafate, gentamicin, sulfisoxazole/phenazopyridine, tobramycin, lincomycin, neomycin/polymyxin B/gramicidin, clindamycin hydrochloride, lansoprazole/clarithromycin/amoxicillin, alatrofloxacin, linezolid, bismuth subsalicylate/metronidazole/tetracycline, erythromycin/benzoyl peroxide, mupirocin, fosfomycin, pentamidine isethionate, imipenem/cilastatin, troleandomycin, gatifloxacin, chloramphenicol, cycloserine, neomycin/polymyxin B/hydrocortisone, ertapenem, meropenem, cephalosporins, fluconazole, cefepime, sulfamethoxazole, sulfamethoxazole/trimethoprim, neomycin/polymyxin B, penicillins, rifampin/isoniazid, erythromycin estolate, erythromycin ethylsuccinate, erythromycin stearate, ampicillin trihydrate, ampicillin/probenecid, sulfasalazine, sulfanilamide, sodium sulfacetamide, dapsone, doxycycline hyclate, trimenthoprim/sulfa, methenamine mandelate, plasmodicides, pyrimethamine, hydroxychloroquine, chloroquine phosphate, trichomonocides, anthelmintics, atovaquone, bacitracin, bacitracin/polymyxin b, gentamycin, neomycin/polymyxin/dexameth, neomycin sulf/dexameth, sulfacetamide/prednisolone, sulfacetamide/phenylephrine, tobramycin sulfate/dexameth, bismuth tribromophenate, silver ion compounds, silver nanoparticles, zerovalent silver, multivalent silver, elemental silver, and silver containing compounds such as silver sulfadiazine and related compounds, gallium ion compounds, gallium ion salst, a gallium ion nanoparticles, alloys of gallium, and alloys of gallium and silver.

In some embodiments, the present invention provides the delivery of antivirals, including, but not limited to, amantadine, acyclovir, foscarnet, indinavir, ribavirin, enfuvirtide, emtricitabine, lamivudine, abacavir sulfate, fomivirsen, valacyclovir, tenofovir, cidofovir, atazanavir, amprenavir, delavirdine mesylate, famciclovir, adefovir, didanosine, efavirenz, trifluridine, inidinavir, lamivudine, vidarabine, lopinavir/ritonavir, ganciclovir, zanamivir, abacavir/lamivudine/zidovudine, lamivudine/zidovudine, nelfinavir, nelfinavir mesylate, nevirapine, ritonavir, saquinavir, saquinavir mesylate, rimantadine, stavudine, docosanol, zalcitabine, idoxuridine, zidovudine, zidovudine/didanosine, valganciclovir, penciclovir, lamivudine, and oseltamivir.

In some embodiments, the present invention provides the delivery of antifungals, including, but not limited to, amphotericin B, nystatin, nystatin/triamcinolone, itraconazole, ketoconazole, miconazole, sulconazole, clotrimazole, clotrimazole/betamethasone, enilconazole, econazole, oxiconazole, tioconazole, terconazole, butoconazole, thiabendazole, flucytosine, butenafine, ciclopirox, haloprogin, naftifine, tolnaftate, natamycin, undecylenic acid, mafenide, dapsone, clioquinol, clioquinol/hydrocortisone, potassium iodide, silver sulfadiazine, gentian violet, carbol-fuchsin, cilofungin, sertaconazole, voriconazole, fluconazole, terbinafine, caspofungin, other topical azole drugs, and griseofulvin.

In some embodiments, the present invention provides the use and delivery of buffering agents, including, but not limited to, Maleic acid, Phosphoric acid, Glycine, Chloroacetic acid, Formic acid, Benzoic acid, Acetic acid, Pyridine, Piperazine, MES, Bis-tris, Carbonate, ACES, ADA MOPSO, PIPES, Phosphoric acid, BES, MOPS, TES, HEPES, DIPSO, TAPSO, Triethanolamine, HEPSO, Tris, Tricine, Bicine, TAPS, Borate, Ammonia, CHES, Ethanolamine, CAPSO, Glycine, Carbonate, CAPS, Methylamine, Piperidine, and Phosphoric acid.

In some embodiments, the present invention provides the delivery of vitamins and minerals, including, but not limited to, Vitamin A, Carotenoids, Vitamin D, Vitamin E, Vitamin K, Vitamin C/ascorbic acid, B1/thiamin, B2/riboflavin, B3/niacin, B5/pantothenic acid, B6/pyridoxine, B12/cobalamin, Biotin, Calcium, Magnesium, Phosphorus, Sodium, Chloride, Potassium, Boron, Chromium, Copper, Iodine, Iron, Manganese, Selenium, and Zinc.

In some embodiments, the present invention provides the delivery of analgesics, including, but not limited to, acetaminophen, anileridine, acetylsalicylic acid, buprenorphine, butorphanol, fentanyl, fentanyl citrate, codeine, rofecoxib, hydrocodone, hydromorphone, hydromorphone hydrochloride, levorphanol, alfentanil hydrochloride, meperidine, meperidine hydrochloride, methadone, morphine, nalbuphine, opium, levomethadyl, hyaluronate sodium, sufentanil citrate, capsaicin, tramadol, leflunomide, oxycodone, oxymorphone, celecoxib, pentazocine, propoxyphene, benzocaine, lidocaine, dezocine, clonidine, butalbital, phenobarbital, tetracaine, phenazopyridine, sulfamethoxazole/phenazopyridine, and sulfisoxazole/phenazopyridine.

In some embodiments, the present invention provides the delivery of local anesthetics (which may also be analgesics as is known in the art), including, but not limited to, amylocaine, ambucaine, articaine, benzocaine, benzonatate, bupivacaine, butacaine, butanilicaine, chloroprocaine, cinchocaine, cyclomehtycaine, dibucaine, diperodon, dimethisoquin, dimethocaine, eucaine, etidocaine, hexylcaine, fomocaine, fotocaine, hydroxyprocaine, isobucaine, levobupivicaine, iodocaine, mepivacaine, meprylcaine, metabutoxycaine, nitracaine, orthocaine, oxetacaine, oxybuprocaine, paraethocycaine, phenacaine, piperocaine, piridocaine, pramocaine, prilocaine, primacaine, procaine, procainamide, proparacaine, propoxycaine, pyrrocaine, quinisocaine, ropivacaine, trimecaine, tetracaine, tolycaine, and tropacocaine.

In some embodiments, the present invention provides the delivery of opioid antagonists and/or mixed opioid agonist/antagonists (which may also be opioid analgesic as is known in the art), including, but not limited to, naloxone, diprenorphine, naltrexone, buprenorphine, bupremorphine/naloxone, nalodeine, nalorphine, levallorphan, nalmefene, naloxol, alvimopan, naldemedine, eluxadoline, asimadoline, naloxegol, methylnaltrexone, dezocine, naloxegol, eptazocine, butorphanol, levorphanol, nalbuphine, pentazocine, phenazocine, cyprodime, naltrindole, norbinaltorphimine, and J113,393.

In some embodiments, the present invention provides the delivery of anticoagulants, including, but not limited to, coumarins, 1,3-indandione, anisindione, fondaparinux, heparin, lepirudin, antithrombin, warfarin, enoxaparin, dipyridamole, dalteparin, ardeparin, nadroparin, and tinzaparin.

In some embodiments, the present invention provides the delivery of coagulation factors, including, but not limited to, Factor I (fibrinogen), Factor II (prothrombin), Factor III (thromboplastin, tissue factor), Factor IV (calcium), Factor V (labile factor), Factor VII (stable factor), Factor VIII (antihemophilic globulin, antihemophilic globulin, antihemophilic factor A), Factor IX (plasma thromboplastin component, Christmas factor, antihemophilic factor B), Factor X (Stuart factor, Prower factor, Stuart-Prower factor), Factor XI (plasma thromboplastin antecedent, antihemophilic factor C), Factor XII (Hageman factor, surface factor, contact factor), and Factor XIII (fibrin stabilizing factor, fibrin stabilizing enzyme, fibri-nase).

In some embodiments, the present invention provides the delivery of anti-inflammatory agents, including, but not limited to, non steroidal anti-inflammatory drugs (NSAIDs) including diclofenac (also known as Voltaren, Abitren, Allvoran, Almiral, Alonpin, Anfenax, Artrites, Betaren, Blesin, Bolabomin, Cataflam, Clofec, Clofen, Cordralan, Curinflam, Diclomax, Diclosian, Dicsnal, Difenac, Ecofenac, Hizemin, Inflamac, Inflanac, Klotaren, Lidonin, Monoflam, Naboal, Oritaren, Remethan, Savismin, Silino, Staren, Tsudohmin, Voltarol, Voren, Voveran, and Vurdon), diflunisal (also known as Dolobid, Adomal, Diflonid, Diflunil, Dolisal, Dolobis, Dolocid, Donobid, Dopanone, Dorbid, Dugodol, Flovacil, Fluniget, Fluodonil, Flustar, Ilacen, Noaldol, Reuflos, and Unisal), etodolac (also known as Lodine), fenoprofen (also known as Nalfon, Fenoprex, Fenopron, Fepron, Nalgesic, and Progesic), flurbiprofen (also known as Ansaid and Ocuflur), ibuprofen (also known as Rufen, Motrin, Aches-N-Pain, Advil, Nuprin, Dolgesic, Genpril, Haltran, Ibifon, Ibren, Ibumed, Ibuprin, Ibupro-600, Ibuprohm, Ibu-Tab, Ibutex, Ifen, Medipren, Midol 200, Motrin-IB, Cramp End, Profen, Ro-Profen, Trendar, Alaxan, Brofen, Alfam, Brufen, Algofen, Brufort, Amersol, Bruzon, Andran, Buburone, Anflagen, Butacortelone, Apsifen, Deflem, Artofen, Dolgit, Artril, Dolocyl, Bloom, Donjust, Bluton, Easifon, Ebufac, Emflam, Emodin, Fenbid, Fenspan, Focus, Ibosure, Ibufen, Ibufug, Ibugen, Ibumetin, Ibupirac, Imbun, Inabrin, Inflam, Irfen, Librofen, Limidon, Lopane, Mynosedin, Napacetin, Nobafon, Nobgen, Novogent, Novoprofen, Nurofen, Optifen, Paduden, Paxofen, Perofen, Proartinal, Prontalgin, Q-Profen, Relcofen, Remofen, Roidenin, Seclodin, Tarein, and Zofen), indomethacin (also known as Indameth, Indocin, Amuno, Antalgin, Areumatin, Argilex, Artherexin, Arthrexin, Artrinovo, Bavilon, Bonidon, Boutycin, Chrono-Indocid, Cidalgon, Confortid, Confortind, Domecid, Durametacin, Elemetacin, Idicin, Imbrilon, Inacid, Indacin, Indecin, Indocap, Indocen, Indocid, Indoflex, Indolag, Indolar, Indomed, Indomee, Indometacinum, Indometicina, Indometin, Indovis, Indox, Indozu, Indrenin, Indylon, Inflazon, Inpan, Lauzit, Liometace, Metacen, Metindon, Metocid, Mezolin, Mobilan, Novomethacin, Peralgon, Reflox, Rheumacid, Rheumacin, Salinac, Servindomet, Toshisan, and Vonum), ketoprofen (also known as Orudis, Alrheumat, Alrheumun, Alrhumat, Aneol, Arcental, Dexal, Epatec, Fastum, Keduril, Kefenid, Keprofen, Ketofen, Ketonal, Ketosolan, Kevadon, Mero, Naxal, Oruvail, Profenid, Salient, Tofen, and Treosin), ketorolac (also known as Toradol), meclofenamate (also known as Meclofen, Meclomen, and Movens), mefenamic acid (also known as Ponstel, Alpain, Aprostal, Benostan, Bonabol, Coslan, Dysman, Dyspen, Ecopan, Lysalgo, Manic, Mefac, Mefic, Mefix, Parkemed, Pondex, Ponsfen, Ponstan, Ponstyl, Pontal, Ralgec, and Youfenam), nabumetone (also known as Relafen), naproxen (also known as Naprosyn, Anaprox, Aleve, Apranax, Apronax, Arthrisil, Artrixen, Artroxen, Bonyl, Congex, Danaprox, Diocodal, Dysmenalgit, Femex, Flanax, Flexipen, Floginax, Gibixen, Headlon, Laraflex, Laser, Leniartil, Nafasol, Naixan, Nalyxan, Napoton, Napren, Naprelan, Naprium, Naprius, Naprontag, Naprux, Napxen, Narma, Naxen, Naxid, Novonaprox, Nycopren, Patxen, Prexan, Prodexin, Rahsen, Roxen, Saritilron, Sinartrin, Sinton, Sutony, Synflex, Tohexen, Veradol, Vinsen, and Xenar), oxaprozin (also known as Daypro), piroxicam (also known as Feldene, Algidol, Antiflog, Arpyrox, Atidem, Bestocam, Butacinon, Desinflam, Dixonal, Doblexan, Dolonex, Feline, Felrox, Fuldin, Indene, Infeld, Inflamene, Lampoflex, Larapam, Medoptil, Novopirocam, Osteral, Pilox, Piraldene, Piram, Pirax, Piricam, Pirocam, Pirocaps, Piroxan, Piroxedol, Piroxim, Piton, Posidene, Pyroxy, Reucam, Rexicam, Riacen, Rosic, Sinalgico, Sotilen, Stopen, and Zunden), sulindac (also known as Clinoril, Aflodac, Algocetil, Antribid, Arthridex, Arthrocine, Biflace, Citireuma, Clisundac, Imbaral, Lindak, Lyndak, Mobilin, Reumofil, Sudac, Sulene, Sulic, Sulindal, Suloril, and Sulreuma), tolmetin (also known as Tolectin, Donison, Midocil, Reutol, and Safitex), celecoxib (also known as Celebrex), meloxicam (also known as Mobic), rofecoxib (also known as Vioxx), valdecoxib (also known as Bextra), aspirin (also known as Anacin, Ascriptin, Bayer, Bufferin, Ecotrin, and Excedrin) and steroidal anti-inflammatory drugs including cortisone, prednisone and dexamethasone.

In some embodiments, the present invention provides the delivery of vasoconstrictors, including, but not limited to, epinephrine (adrenaline, Susphrine), phenylephrine hydrochloride (Neo-Synephrine), oxymetazoline hydrochloride (Afrin), norepinephrine (Levophed), and caffeine.

In some embodiments, the present invention provides the delivery of vasodilators, including, but not limited to, bosentan (Tracleer), epoprostenol (Flolan), treprostinil (Remodulin), sitaxsentan, nifedipine (Adalat, Procardia), nicardipine (Cardene), verapamil (Calan, Covera-HS, Isoptin, Verelan), diltiazem (Dilacor XR, Diltia XT, Tiamate, Tiazac, Cardizem), isradipine (DynaCirc), nimodipine (Nimotop), amlodipine (Norvasc), felodipine (Plendil), nisoldipine (Sular), bepridil (Vascor), hydralazine (Apresoline), minoxidil (Loniten), isosorbide dinitrate (Dilatrate-SR, Iso-Bid, Isonate, Isorbid, Isordil, Isotrate, Sorbitrate), isorbide mononitrate (IMDUR), prazosin (Minipress), cilostazol (Pletal), treprostinil (Remodulin), cyclandelate, isoxsuprine (Vasodilan), nylidrin (Arlidin), nitrates (Deponit, Minitran, Nitro-Bid, Nitrodisc, Nitro-Dur, Nitrol, Transderm-Nitro), benazepril (Lotensin), benazepril and hydrochlorothiazide (Lotensin HCT), captopril (Capoten), captopril and hydrochlorothiazide (Capozide), enalapril (Vasotec), enalapril and hydrochlorothiazide (Vaseretic), fosinopril (Monopril), lisinopril (Prinivil, Zestril), lisinopril and hydrochlorothiazide (Prinzide, Zestoretic), moexipril (Univasc), moexipril and hydrochlorothiazide (Uniretic), perindopril (Aceon), quinapril (Accupril), quinapril and hydrochlorothiazide (Accuretic), ramipril (Altace), trandolapril (Mavik), papaverine (Cerespan, Genabid, Pavabid, Pavabid HP, Pavacels, Pavacot, Pavagen, Pavarine, Pavased, Pavatine, Pavatym, Paverolan).

In some embodiments, the present invention provides the delivery of diuretics, including, but not limited to, acetazolamide (Diamox), dichlorphenamide (Daranide), methazolamide (Neptazane), bendroflumethiazide (Naturetin), benzthiazide (Exna), chlorothiazide (Diuril), chlorthalidone (Hygroton), hydrochlorothiazide (Esidrix, HydroDiuril, Microzide), hydroflumethiazide (Diucardin), indapamide (Lozol), methyclothiazide (Enduron), metolazone (Zaroxolyn, Mykrox), polythiazide (Renese), quinethazone (Hydromox), trichlormethiazide (Naqua), bumetanide (Bumex), ethacrynic acid (Edecrin), furosemide (Lasix), torsemide (Demadex), amiloride (Midamor), amiloride and hydrochlorothiazide (Moduretic), spironolactone (Aldactone), spironolactone and hydrochlorothiazide (Aldactazide), triamterene (Dyrenium), triamterene and hydrochlorothiazide (Dyazide, Maxzide).

In some embodiments, the present invention provides the delivery of anti-cancer agents, including, but not limited to, aldesleukin, alemtuzumab, alitretinoin, allopurinol, altretamine, amifostine, anagrelide, anastrozole, arsenic trioxide, asparaginase, bexarotene, bicalutamide, bleomycin, busulfan, calusterone, capecitabine, carboplatin, carmustine, celecoxib, chlorambucil, cisplatin, cladribine, cyclophosphamide, cytarabine, dacarbazine, dactinomycin, darbepoetin alpha, daunorubicin, daunomycin, dexrazoxane, docetaxel, doxorubicin, epoetin alpha, estramustine, etoposide, etoposide phosphate, exemestane, filgrastim, floxuridine, fludarabine, flutamide, fulvestrant, gemcitabine, gemtuzumab ozogamicin, goserelin acetate, hydroxyurea, ibritumomab tiuxetan, idarubicin, ifosfamide, imatinib mesylate, interferon alpha-2a, interferon alpha-2b, irinotecan, leflunomide, letrozole, leucovorin, levamisole, lomustine, meclorethamine (nitrogen mustard), megestrol acetate, melphalan, mercaptopurine, mesna, methotrexate, methoxsalen, mitomycin C, mitotane, mitoxantrone, mycophenolate mofetil, nandrolone phenpropionate, nilutamide, nofetumomab, oprelvekin, oxaliplatin, paclitaxel, pamidronate, pegademase, pegaspargase, pegfilgrastim, pentostatin, pipobroman, plicamycin, porfimer sodium, procarbazine, quinacrine, rasburicase rituximab, sargramostim, streptozocin, tacrolimus, tamoxifen, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In other embodiments, the bioactive agent is an siRNA. The RNAi constructs of the present invention are gene(s) that express RNAs that base pair to form a dsRNA RNA region. The RNAs may be a part of the same molecule or different molecules. In preferred embodiments, the RNAi construct comprises a promoter operably linked to a nucleic acid sequence encoding two complementary sequences separated by a loop sequence. The complementary regions correspond to a target RNA sequence separated by a loop sequence. When the RNAi construct is expressed, the complementary regions of the resulting RNA molecule pair with one another to form a double stranded RNA region. The present invention is not limited to loop sequences of any particular length. In some preferred embodiments, the loop sequences range from about 4 to about 20 nucleotides in length. In more preferred embodiments, the loop sequences are from about 6 to about 12 nucleotides in length. In other preferred embodiments, the dsRNA regions are from about 19 to about 23 in length.

In other embodiments, the dsRNA is formed from RNA transcribed from a vector as two separate stands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. In some embodiments, a DNA duplex provided at each end with a promoter sequence can directly generate RNAs of defined length, and which can join in pairs to form a dsRNA. See, e.g., U.S. Pat. No. 5,795,715, incorporated herein by reference. RNA duplex formation may be initiated either inside or outside the cell.

It will be recognized that after processing the resulting siRNA can comprise two blunt ends, one blunt end and one end with an overhang, or two ends with overhangs. In some embodiments, the end or ends with overhangs comprise an overhang of either one or two nucleotides. As a non-limiting example, a siRNA of 23 nucleotides in length comprises two 19mers with a two nucleotide overhang at each end. As another non-limiting example, a siRNA of 21 nucleotides in length comprises two 19mers with a single nucleotide overhang at each end. As still another non-limiting example, a siRNA of 22 nucleotides in length comprises two 22mers with no overhangs at either end.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

There is no upper limit on the length of the dsRNA that can be used. For example, the dsRNA can range from about 21 base pairs (bp) of the gene to the full length of the gene or more. In one embodiment, the dsRNA used in the methods of the present invention is about 1000 bp in length. In another embodiment, the dsRNA is about 500 bp in length. In yet another embodiment, the dsRNA is about 22 bp in length. In some preferred embodiments, the sequences that mediate RNAi are from about 21 to about 23 nucleotides. The isolated iRNAs of the present invention mediate degradation of the target RNA.

The double stranded RNA of the present invention need only be sufficiently similar to natural RNA that it has the ability to mediate RNAi for the target RNA. In one embodiment, the present invention relates to RNA molecules of varying lengths that direct cleavage of specific mRNA to which their sequence corresponds. It is not necessary that there be perfect correspondence of the sequences, but the correspondence must be sufficient to enable the RNA to direct RNAi cleavage of the target mRNA. In a particular embodiment, the RNA molecules of the present invention comprise a 3' hydroxyl group.

E. Medical Devices

In some embodiments, the present invention provides a freestanding microsheet of a desired size and shape as described above, preferably comprising a bioactive compound (e.g., antimicrobial silver compounds, antimicrobial gallium compounds, or analgesic compounds). The microsheet may preferably be provided in a desired size and shape by cutting the substrate material to a desired size and shape and peeling the microsheet from the substrate. The microsheet may then be applied to a biological surface such as a wound or a medical surface such as the surface of a medical device such as wound covering.

In some embodiments, the microsheet is used to modify a wound dressing or biologic wound dressing that is compatible with functionalization by addition of a matrix material. Examples of commercially available wound dressings that can be modified by addition of a microsheet include, but are not limited to, Biobrane™, gauze, adhesive tape, bandages such as Band-Aids®, and other commercially available wound dressings including but not limited to COMPEEL®, DUODERM™, TAGADERM™, and OPSITE®. In some embodiments, the present invention provides methods for transferring a polymer multilayer to a desired surface, such as soft surface. Such soft surfaces include, but are not limited to, skin, a wound bed, a tissue, artificial tissues including artificial skin tissues such as organotypically cultured skin tissues, Apligraf®, Dermagraft®, Oasis®, Transcyte®, Cryoskin® and Myskin®, artificial tissue matrices, gels comprising biomolecules, a wound dressing, and a biologic wound dressing. In some embodiments, the desired surface is contacted with a polymer multilayer, e.g., a polymer multilayer supported on a support and pressure is applied to effect transfer of the polymer multilayer from the support to the desired surface. In some embodiments, the pressure is from about 10 to about 500 kPa. In some embodiments, the transfer is performed in the substantial, or complete, absence of solution. Such dry transfer processes do not involve exposure of biological components of the desired surface to aqueous solutions containing species that may influence the activity of the biological components. In some embodiments, the transfer is performed through a gas phase. In some embodiments, the transfer is performed in an environment where the humidity is less than 100% of saturation. In some embodiments, the transfer is performed in the absence of liquid water.

Accordingly, in some embodiments, the present invention provides wound dressings comprising a support material having a surface oriented to a wound, wherein the surface oriented to the wound is modified with a microsheet material of the present invention. When applied to a wound, the surface of the support material modified with the matrix material is put into contact with the wound bed.

In some embodiments, the support is a biologic wound dressing. In some embodiments, the biologic wound dressing is a type of wound dressing that comprises, e.g., is coated with or incorporates, cells (e.g., keratinocytes or fibroblasts and combinations thereof) and/or one or more biomolecules or fragments of biomolecules that can be placed in contact with the wound surface. The biomolecules may be provided in the form of an artificial tissue matrix comprising one or more biomolecules. Examples of such biomolecules include, but are not limited, to collagen, glycosaminoglycans, hyaluronic acid, laminin, vitronectin, fibronectin, keratin, antimicrobial polypeptides and combinations thereof. Examples of suitable biologic wound dressings include, but are not limited to, BIOBRANE™, Integra™, Apligraf®, Dermagraft®, Oasis®, Transcyte®, Cryoskin® and Myskin®.

In some embodiments, the microsheets are sued to modify a biosynthetic wound dressing constructed of an elastomeric film (e.g., a silicone film) supported on support material, such as a fabric, preferably a polymeric fabric such as a nylon fabric. In some embodiments, the fabric is at least partially imbedded into the film (e.g., BioBrane™). In some embodiments, the elastomeric film is coated with one or more biomaterials, for example collagen, keratin, fibronectin, vitronectin, laminin and combinations thereof Accordingly, the fabric presents to the wound bed a complex 3-D structure to which a biomaterial (e.g., collagen) has been bound, preferably chemically bound. In some preferred embodiments, the surface presented to the wound is further modified with a microsheet material as described above. In some preferred embodiments, the microsheet material is a polyelectrolyte membrane comprising a bioactive agent, preferably selected from one or more of silver nanoparticles, elemental silver, and silver containing compounds such as silver sulfadiazine and/or gallium ions and related compounds, and preferably included in the concentration ranges described above. In some embodiments, the microsheet further comprises nanoscale or microscale particles.

In some embodiments, the microsheet is used to modify an adhesive bandage comprising an adhesive portion (such as an adhesive strip) and an absorbent material, preferably treated or coated with a material (i.e., a non-adherent material) to prevent adhesion to the wound or comprising a layer of non-adherent material, such as Teflon®, on the surface of the absorbent pad that will contact the wound. In some embodiments, the support material is an absorbent pad (e.g., a gauze pad or polymer foam) preferably treated or coated with a material (i.e., a non-adherent material) to prevent adhesion to the wound or comprising a layer of non-adherent material, such as Teflon® or other suitable material, on the surface of the absorbent pad that will contact the wound. In some embodiments, the non-adhesive material or layer is breathable. In some embodiments, the wound dressing comprises a gel-forming agent, for example, a hydrocolloid such as sodium carboxymethylcellulose. In some embodiments, the absorbent pads or gel-forming agents are affixed to a material that is waterproof and/or breathable. Examples include, but are not limited, semipermeable polyurethane films. The waterproof and/or breathable material may further comprise an adhesive material for securing the bandage to the skin of a subject. The waterproof and/or breathable material preferably forms the outer surface of the adhesive bandage or pad, i.e., is the surface opposite of the surface comprising the matrix which contacts the wound. Examples of such adhesive bandages and absorbent pads include, but are not limited to, to adhesive bandages and pads from the Band-Aid® line of wound dressings, adhesive bandages and pads from the Nexcare® line of wound dressings, adhesive bandages and non-adhesive pads from the Kendall Curity Tefla® line of wound dressings, adhesive bandages and pads from the Tegaderm® line of wound dressings, adhesive bandages and pads from the SteriStrip® line of wound dressings, the COMFEEL® line of wound dressings, adhesive bandages and pads, the Duoderm® line of wound dressings, adhesive bandages and pads, the TEGADERM™ line of wound dressings, adhesive bandages and pads, the OPSITE® line of wound dressings, adhesive bandages and pads, adhesive bandages and pads from the Allevyn™ line of wound dressings, adhesive bandages and pads from the Duoderm® line of wound dressings, and adhesive bandages and pads from the Xeroform® line of wound dressings.

In some embodiments, the nanoscale polymer matrix is used to modify a medical device such as a surgical mesh. Examples of commercially available surgical meshes that can be modified by addition of a matrix as described below include, but are not limited to, polypropyelene, polyester, polytetrafluoroethylene meshes, or absorbable biomeshes, or biological meshes (biomeshes), including but not limited to ULTRAPRO™ mesh, PROCEED™ mesh, PROLENE™ polypropyelene mesh, Ethicon Physiomesh™, MERSILENE™ polyester mesh, PARIETEX™ mesh, DOLPHIN™ polypropylene mesh, GORE INFINIT™ mesh, PERFIX™, KUGEL™, 3DMAX™, BARD™, VISILEX™, XENMATRIX™, ALLOMAX™, SURGISIS BIODESIGN™, and TIGR MATRIX™.

G. Use of Matrices

In some embodiments, a microsheet as described above is applied to a wound under conditions such that wound healing, as measured by wound contraction, is accelerated. In some embodiments of the invention, the microsheet containing one or more bioactive agents is transferred to a wound or tissue so that the sacrificial polymer layer lies on top of the nanoscale polymer layer after transfer to the wound or tissue. In some embodiments, a wound dressing is placed on top of the sacrificial polymer layer before or after the sacrificial polymer layer is dissolved or partially dissolved in an aqueous liquid. In some embodiments, a nanoscale polymer matrix made with PEMs containing one or more bioactive agents and a dissolvable sacrificial second polymer layer is transferred to a wound or tissue surface such that sacrificial layer dissolves completely in wound and PEMs are in direct contact with the wound tissue and a primary/secondary wound dressing placed over the wound. In some embodiments, the primary dressing is a biologic dressing and the nanoscale polymer matrix does not hinder integration of biologic dressing in the wound-bed.

In some embodiments, the microsheets are provided as kits, preferably with the microsheet in a sterile package. In some embodiments the microsheet provided in the kit comprises at least one bioactive agent. In other embodiments, the kits comprise a bioactive agent and instructions from applying the bioactive agent to the matrix prior to application to a wound.

A microsheet with one or more bioactive agents, as described above, can be applied to all types of wounds. Furthermore, a wound modifying agent with one or more bioactive agents can be applied to skin, mucous membranes, body cavities, and to internal surfaces of bones, tissues, etc. that have been damaged. A microsheet with one or more bioactive agents can be used on wounds such as cuts, abrasions, ulcers, surgical incision sites, burns, and to treat other types of tissue damage. In some embodiments of the present invention, the microsheets enhance wound healing. The present invention contemplates that wound healing may be enhanced in a variety of ways. In some embodiments, the compositions and methods minimize contracture of the wound as to best favor function and cosmesis. In some embodiments, compositions and methods promote wound contracture to best favor function and cosmesis. In some embodiments, the compositions and methods promote vascularization. In some embodiments, the compositions and methods inhibit vascularization. In some embodiments, the compositions and methods promote fibrosis. In some embodiments, the compositions and methods inhibit fibrosis. In some embodiments, the compositions and methods promote epithelial coverage. In some embodiments, the compositions and methods inhibit epithelial coverage. In some embodiments, the compositions and methods of the present invention modulates one or properties of cells in the wound environment or in the immediate vicinity of the wound. The properties that are modulated, e.g., are increased or decreased, include, but are not limited to adhesion, migration, proliferation, differentiation, extracellular matrix secretion, phagocytosis, MMP activity, contraction, and combinations thereof. The microsheets of the present invention can be covered with a secondary dressing, or bandage, if desired to protect the layer or to provide additional moisture absorption, for example.

EXPERIMENTAL

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. The examples are not intended to restrict the scope of the invention.

Example 1

A. Coating and Release

Materials.
1. 20 mM solution of polycation (polyallylamine hydrochloride, PAH) at pH=6.8-7.2.
2. 20 mM solution of polyanion (polyacrylic acid, PAA) at pH=2.1-2.3.
3. 10 mM solution of active agent (silver nitrate).
4. 1 mM solution of reducing agent (sodium borohydride).
5. 21% aqueous solution of polyvinyl alcohol on weight basis.
6. A flexible polymeric sheet of thickness 1-10 mil (1 mil=1/1000 inch) pre-coated with a release layer as substrate for depositing polyelectrolyte multilayers.

Procedure.
1. Coat a polyelectrolyte multilayer comprising of 10 bilayers of PAH and PAA via layer-by-layer assembly by incubating the substrate in aqueous solutions of PAH and PAA for 6 min each mediated by rinsing and drying after each incubation step.
2. Load silver into polyelectrolyte multilayer coating by
   a. Incubating polyelectrolyte multilayer supported on the substrate in silver nitrate solution for 30 min followed by rinsing with water and drying. Incubate in sodium borohydride solution for 1 min followed by rinsing.
   b. Repeat (a.)
   c. Incubating polyelectrolyte multilayer supported on the substrate in silver nitrate solution for 30 min followed by rinsing with water and drying.
3. Cast a 20 µm (dry thickness) PVA film over silver loaded polyelectrolyte multilayer supported on the substrate
4. Obtain a freestanding film by peeling the coating off the substrate.

Results.

Each substrate was evaluated based on the following Yes/No tests and the results are documented in the table below:
1. Based on visual inspection, did polyelectrolyte multilayer coating detach partially or completely from the substrate after the completion of Procedure step #1?
2. Based on visual inspection, did polyelectrolyte multilayer coating detach partially or completely from the substrate after the completion of Procedure step #2?
3. Based on visual inspection, did polyelectrolyte multilayer coating transfer completely from the substrate to PVA coating after the completion of Procedure step #4?

| Substrate | PEM Coating Detachment (Yes/No/Slight) | Silver loading Detachment (Yes/No/Slight) | Peeling and Complete Transfer without Tears (Yes/No/Slight) |
|---|---|---|---|
| 3M ™ Scotchpak ™ 9742 Release Liner Linear Release < 100 g/in* | No | No | No |
| 3M ™ Scotchpak ™ 1022 Release Liner Linear Release < 100 g/in* | No | No | No |
| 3M ™ Scotchpak ™ 9744 Release Liner Linear Release < 100 g/in* | No | No | No |
| 3M ™ Scotchpak ™ 9755 Release Liner Linear Release < 40 g/in* | No | No | No |
| Saint Gobain 4130 Release Coating Liner Release < 10 g/in** | No | No | Yes |
| Saint Gobain 4150 Release Coating Liner Release N/A | No | Slight | Yes |
| Saint Gobain 8711 Release Coating Liner Release < 15-50 g/in** | No | No | Yes |
| Saint Gobain 7819 Release Coating Liner Release < 10 g/in** | No | No | Yes |
| Pass Criteria | No | No | Yes |

*Test method not available
**Saint Gobain Test #125 Wet Spread Release

B. Process

Materials
1. 20 mM solution of polycation (polyallylamine hydrochloride, PAH, 150 kDa) at pH=6.8-7.2. (unless otherwise noted)
2. 20 mM solution of polyanion (polyacrylic acid, PAA, 100 kDa) at pH=2.1-2.3. (unless otherwise noted)
3. S mM solution of active agent (silver nitrate).
4. R mM solution of reducing agent (sodium borohydride).
5. 21.25% aqueous solution of polyvinyl alcohol.
6. A flexible polymeric sheet pre-coated with a release layer as substrate for depositing polyelectrolyte multilayers.

Procedure
1. Coat a polyelectrolyte multilayer comprising of N bilayers of PAH and PAA via layer-by-layer assembly by incubating the substrate in aqueous solutions of PAH and PAA for Xs (or min) each mediated by rinsing and drying after each incubation step.
2. Load silver into polyelectrolyte multilayer coating by
   a. Incubating polyelectrolyte multilayer supported on the substrate in silver nitrate solution for Y s (or min) followed by rinsing with water and drying. Incubate in sodium borohydride solution for 1 min followed by rinsing.
   b. Repeat (a.) n times
   c. Incubating polyelectrolyte multilayer supported on the substrate in silver nitrate solution for Y s (or min) followed by rinsing with water and drying.
3. Measure silver loading in the films by extracting silver from films into nitric acid and analyzing the extract using Inductively Coupled Plasma-Optical Emission Spectroscopy (ICP-OES).

Results

1. Y=30 min, N=10, n=2, R=1 mM

TABLE

Silver loading (μg/cm²) in polyelectrolyte multilayers:

| | Silver Loading | | |
|---|---|---|---|
| S | X = 10 s | X = 30 s | X = 1 min |
| 10 mM | 5.8 ± 0.5 | 5.7 ± 0.5 | 5.7 ± 0.7 |
| 100 mM | 6.4 ± 0.6 | 7.0 ± 0.5 | 7.2 ± 0.5 |

2. X=6 min, n=2, R=1 mM

TABLE

Silver loading (μg/cm²) in polyelectrolyte multilayers:

| | | Silver Loading | | |
|---|---|---|---|---|
| S | N | Y = 1 min | Y = 8 min | Y = 60 min |
| 10 mM | 10 | 8.24 ± 0.3 | 7.2 ± 0.3 | 9.1 ± 0.2 |
| 100 mM | 4 | N/A | 2.3 ± 0.1 | 2.5 ± 0.2 |
| 100 mM | 10 | 9.2 ± 1.4 | 10.6 ± 0.8 | 11.4 ± 0.2 |

3. X=6 min,

TABLE

| | Silver loading (μg/cm$^2$) in polyelectrolyte multilayers: | | | |
|---|---|---|---|---|
| N | S | R | n | Silver Loading Y = 20 min |
| 20 | 10 mM | 1 mM | 1 | 10.9 |
| 20 | 10 mM | 10 mM | 1 | 12.4 |
| 15 | 10 mM | 1 mM | 2 | 9.5 |
| 15 | 10 mM | 10 mM | 2 | 15.8 |
| 10 | 10 mM | 10 mM | 4 | 16.0 |

4. X=6 min, Y=60 min, N=10, n=2, S=10 mM, R=1 mM, Mw PAH=150 kDa

TABLE

| Silver loading (μg/cm$^2$) in polyelectrolyte multilayers: | | |
|---|---|---|
| Mw PAA (5 kDa) | Mw PAA (100 kDa) | Silver Loading |
| 100% (w/w) | 0% (w/w) | 8.62 ± 0.62 |
| 0% (w/w) | 100% (w/w) | 6.41 ± 0.53 |
| 70% (w/w) | 30% (w/w) | 17.79 ± 0.44 |
| 30% (w/w) | 70% (w/w) | 7.99 ± 0.89 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

What is claimed is:

1. An article comprising:
   a flexible substrate in communication with a roll, the flexible substrate having a surface comprising a release coating selected from a silicone coating, a polydimethyl siloxane (PDMS) coating, a fluorocarbon coating, a polyacrylate coating, a polystyrene coating, a polystyreneacrylic coating, a chromium stearate complex coating, and a polyolefin coating and having a total surface area greater than 0.65 square meters;
   a nanoscale polymer multilayer adjacent to and in contact with the surface, the nanoscale polymer multilayer having a thickness of from 0.5 nm to 10000 nm thick, and
   a sacrificial polymer layer adjacent to and in contact with the nanoscale polymer multilayer so that the nanoscale polymer multilayer is between the surface of the substrate and the sacrificial polymer layer and wherein the sacrificial polymer layer is dissolvable or biodegradable, and is from 0.2 μm to 1000 μm thick,
   wherein the article further comprises a bioactive agent incorporated into the nanoscale polymer multilayer, wherein the bioactive agent is interspersed within the three dimensional structure of the nanoscale polymer multilayer or interspersed within the layers of the polymer multilayer and wherein the bioactive agent is selected from the group consisting of an antimicrobial agent, an antibiofilm agent, a growth factor, a hemostatic agent, a bioactive peptide, a bioactive polypeptide, an analgesic, a local anesthetic, an opioid, an opioid antagonist or mixed agonist/antagonist, an anticoagulant, anti-inflammatory agent, and a drug molecule or a drug compound.

2. The article according to claim 1, wherein the nanoscale polymer multilayer comprises alternating layers of at least one positively charged polyelectrolyte and at least one negatively charged polyelectrolyte.

3. The article according to claim 2, wherein the at least one positively charged polyelectrolyte is selected form the group consisting of poly (allylamine hydrochloride) (PAH), polyl-lysine (PLL), poly(ethylene imine) (PEI), poly(histidine), poly(N,N-dimethyl aminoacrylate), poly(N,N,N-trimethylaminoacrylate chloride), poly(methyacrylamidopropyltrimethyl ammonium chloride), and natural or synthetic polysaccharides, or wherein said at least one negatively charged polyelectrolyte is selected from the group consisting of poly (acrylic acid) (PAA), poly (styrenesulfonate) (PSS), alginate, hyaluronic acid, heparin, heparan sulfate, chondroitin sulfate, dextran sulfate, poly (methacrylic acid), oxidized cellulose, carboxymethyl cellulose, polyaspartic acid, and polyglutamic acid.

4. The article according to claim 2, wherein said nanoscale polymer multilayer is formed by applying said at least one positively charged polyelectrolyte and at least one negatively charged polyelectrolyte by a method selected from the group consisting of spray coating, dip coating, immersion coating, spin coating, slot die coating, inkjet coating, anilox coating, screen coating, offset lithography printing, flexographic coating, gravure coating, rotogravure coating, reverse roll coating, metering (Meyer) rod coating, blade coating, knife over roll coating, air knife coating, curtain coating, melt extrusion coating, solvent casting and any combinations thereof.

5. The article according to claim 1, wherein the sacrificial polymer layer decreases the release of bioactive agent from nanoscale multilayer by 1 to 1000 times.

6. The article according to claim 1, wherein the sacrificial polymer layer comprises a polymer selected from the group consisting of polyvinyl alcohol (PVA), polyacrylic acid (PAA), polyvinylpyrrolidone (PVP), carboxymethyl cellulose (CMC), hydroxypropyl cellulose, hydroxypropyl methylcellulose, methylcellulose, ethylcellulose, hydroxyethyl cellulose (HEC), alginates, polyvinylacetate (PVAc), polylactic acid (PLA), polylactic-co-glycolic acid (PLGA), polyglycolic acid, and a polyanhydride.

\* \* \* \* \*